United States Patent [19]
Kishimoto et al.

[11] Patent Number: 5,892,048
[45] Date of Patent: Apr. 6, 1999

[54] TRIAZOLE COMPOUNDS AND PEST CONTROL AGENT

[75] Inventors: Takashi Kishimoto; Yasuo Yamada; Takao Iwasa; Michihiko Matsuda; Renpei Hatano, all of Kanagawa, Japan

[73] Assignee: Nippon Soda Co., Ltd., Tokyo, Japan

[21] Appl. No.: 605,107

[22] PCT Filed: Jun. 30, 1995

[86] PCT No.: PCT/JP95/01314

§ 371 Date: May 6, 1996

§ 102(e) Date: May 6, 1996

[87] PCT Pub. No.: WO96/01257

PCT Pub. Date: Jan. 18, 1996

[30] Foreign Application Priority Data

Jul. 1, 1994 [JP] Japan .................................. 6-173304
Feb. 13, 1995 [JP] Japan .................................. 7-047846

[51] Int. Cl.[6] .................................................. C07D 401/12
[52] U.S. Cl. .......................................................... 546/272.4
[58] Field of Search ........................................... 546/272.4

[56] References Cited

U.S. PATENT DOCUMENTS

| 4,414,221 | 11/1983 | Parsons et al. ...................... | 548/269.4 |
| 5,482,951 | 1/1996 | Ozaki et al. .............................. | 514/340 |
| 5,616,594 | 4/1997 | Ikeda et al. .............................. | 514/340 |

OTHER PUBLICATIONS

Cram and Hammond, "Organic Chemistry", McGraw–Hill Book Co., NY, 2nd Ed. pp. 565–67.

*Primary Examiner*—Patricia L. Morris
*Attorney, Agent, or Firm*—Joseph C. Mason, Jr.

[57] ABSTRACT

This Invention concerns a triazole compound represented by the formula [I] or a salt thereof and a method for the production thereof.

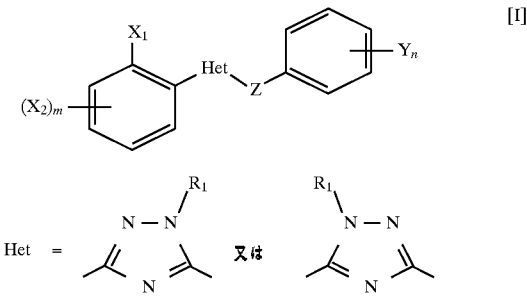

[wherein $X_1$ stands for halogen atoms, $C_1$–$C_6$ alkyl groups, $C_1$–$C_6$ alkoxy groups, $C_1$–$C_6$ haloalkyl groups, etc., $X_2$ stands for halogen atoms, $C_1$–$C_6$ alkyl groups, or $C_1$–$C_6$ alkoxy groups, Y stands for halogen atoms, $C_1$–$C_{12}$ alkyl groups, $C_1$–$C_6$ haloalkyl groups, phenyl group optionally containing a substituent, etc.

$R_1$ stands for $C_1$–$C_6$ alkyl groups, $C_2$–$C_6$ alkenyl groups, $C_2$–$C_6$ alkinyl groups, etc. Z stands for —$CR_2R_3$—, —$CH_2D$—, or —CH=CH—, $R_2$ and $R_3$ independently stand for hydrogen atom, halogen atoms, hydroxy group, etc., D stands for $CH_2$, CO, O, or S, m stands for an integer in the range of 0–4, and n stands for an integer from 0 to 5].

The compounds in accordance with this invention manifest outstanding effects for killing such harmful organisms as harmful insects and mites and are useful as pesticides for agriculture and horticulture.

1 Claim, No Drawings

TRIAZOLE COMPOUNDS AND PEST CONTROL AGENT

TECHNICAL FIELD

This invention relates to a novel triazole compound and a pesticide.

BACKGROUND ART

A host of insecticides and acaricides have been heretofore used. It is not a few of them that hardly deserve to be called completely satisfactory pesticides because they are deficient in effect, because they find only limited use owing to the problem of growing tolerance on the part of pests to be controlled, because they do harm to or contaminate economic plants to be protected, or because they manifest unduly high toxicity to men, beasts, and fish inhibiting the districts in which they are used. Thus, the desirability of developing a chemical reagent that suffers only sparingly from such drawbacks as mentioned above and ensures safe use has been finding enthusiastic recognition.

As a substance which is associated with this invention, the compound of the following formula is disclosed in Bull, Chem. Soc. Jpn., 56, 545 (1983).

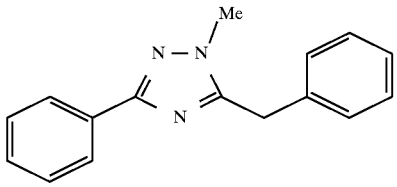

And the compound of the following formula is also disclosed in Journal of Pharmacy, 94 (1), 55 (1974).

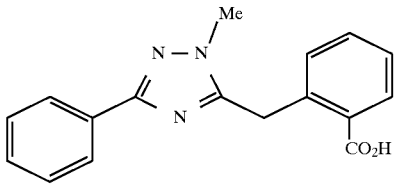

The relevant monograph of this publication, however, has no mention of the compound possesing an insecticidal or acaricidal effect.

DISCLOSURE OF THE INVENTION

An object or this invention is to provide a pesticide which produces a necessary effect infallibly and ensures safe use.

This invention consists in a triazole compound represented by the formula [1]:

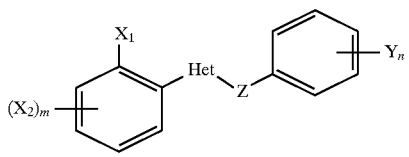

-continued

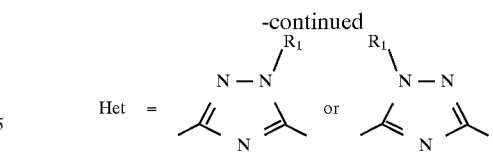

[wherein $X_1$ stands for a halogen atom such as fluorine, chlorine, bromine, and iodine, a $C_1$–$C_6$ alkyl group such as methyl, ethyl, propyl, isopropyl, butyl, s-butyl, t-butyl, i-butyl, pentyl, neopentyl, isoamyl, and hexyl, a $C_1$–$C_6$ alkoxy group such as methoxy, ethoxy, propoxy, isopropoxy, butoxy, i-butoxy, s-butoxy, t-butoxy, pentyloxy, and hexyloxy, a $C_1$–$C_6$ haloalkyl group such as chloromethyl, trifluoromethyl, difluoromethyl, trichloromethyl, chloromethyl, dichloromethyl, trifluoroethyl, pentafluoroethyl, bromomethyl, dibromomethyl, tribromomethyl, perfluoropentyl, and perfluorohexyl, a $C_1$–$C_6$ alkylthio group such as methylthio, ethylthio, propylthio, isopropylthio, butylthio, s-butylthio, t-butylthio, i-butylthio, pentylthio, neopentylthio, isoamylthio, and hexylethylthio, nitro group, a $C_1$–$C_6$ alkylamino group such as methylamino, ethylamino, propylamino, isopropylamino, butylamino, s-butylamino, t-butylamino, i-butylamino, pontylamino, neopentylamino, isoamylamino, and hexylamino, or a $C_1$–$C_6$ dialkylamino group such as dimethylamino, diethylamino, methylethylamino, ethylpropylamino, ethylisopropylamino, dipro-pylamino, diisopropylamino, dibutylamino, di-sec-butylamino, di-t-butylamino, di-i-butylamino, dipentylamino, dineopentylamino, diisoamylamino and dihexylamino.

$X_2$ stands for a halogen atom such as fluorine, chlorine, bromine, and iodine, a $C_1$–$C_6$ alkyl group such as methyl, ethyl, propyl, isopropyl, butyl, s-butyl, t-butyl, i-butyl, pentyl, neopentyl, isoamyl and hexyl, or a $C_1$–$C_6$ alkoxy group such as methoxy, ethoxy, propoxy, isopropoxy, butoxy, i-butoxy, s-butoxy, t-butoxy, pentyloxy, and hexyloxy.

Y stands for a halogen atom such as fluorine, chlorine, bromine and iodine, a $C_1$–$C_{12}$ alkyl group such as methyl, ethyl, propyl, isopropyl, butyl, s-butyl, t butyl, i-butyl, pentyl, neopentyl, isoamyl, hexyl, heptyl, octyl, nonyl, decyl, undecyl, and dodecyl, a $C_1$–$C_6$ haloalkyl group such as fluoromethyl, trifluoromethyl, difluoromethyl, trichloromethyl, chloromethyl, dichloromethyl, trifluoroethyl, pentafluoroethyl, bromomethyl, dibromomethyl, tribromomethyl, perfluoropentyl and perfluorohexyl, a $C_1$–$C_{12}$ alkoxy group such as methoxy, ethoxy, propoxy, isopropoxy, butoxy, i-butoxy, s-butoxy, t-butoxy, pentyloxy, and hdxyloxy (which may be substituted with a halophenyl group), a $C_1$–$C_6$ haloalkoxy group such as trifluoromethoxy and trichloromethoxy, a $C_3$–$C_8$ cycloalkyloxy group such as cyclopropyl, cyclo-propyl, cyclopentyl, cyclohexyl, and cycloheptyl, a $C_1$–$C_6$ alkylthio group such as methylthio, ethylthio, propylthio, isopropylthio, butylthio, s-butylthio, t-butylthio, i-butylthio, pentylthio, neopentylthio, isoamylthio and hexylethylthio, a $C_1$–$C_6$ alkylamino group such is methylamino, ethylamino, propyl-amino, isopropylamino, butylamino, s-butylamino, t-butylamino, i-butylamino, pentylamine, neopentylamino, isoamylamino and hexylamino, a $C_1$–$C_6$ dialkylamino group such as dimethylamino, diethylamino, methylethylamino, ethylpropylamino, ethylisopropyl-amino dipropylamino, diisopropylamino, dibutylamino, di-s-butyl-amino, di-t-butylamino, di-i-butylamino, dipentylamino, dineopen-tylamino, diisoamylamino and dihexylamino, hydroxy group, mercapto group, a $C_1$–$C_6$ alkylcarbonyloxy group such as acetoxy, ethylcarbonyloxy, propylcarbonyloxy, and isopropylcarbonyloxy, a $C_1$–$C_6$ alkylcarbonylthio group such methylcarbonylthio, ethyl carbonylthio, propylcarbonylthio, and isopropylcarbonylthio, a $C_1$–$C_6$ alkoxycarbonyl group such as methoxycarbonyl, ethoxycarbonyl, propoxycarbonyl, isopropoxycarbonyl, and butoxycarbonyl, nitro group or cyano group, optionally substituted phenyl group, optionally substituted phenylmethyl group, optionally substituted phenoxy group, optionally substituted pyridyloxy group, optionally substituted phenylthio group, optionally substituted pyridylthio group, optionally substituted phenylcarbonyloxy group, optionally substituted phenylcarbonylthio group, optionally substituted α-naphthyl group, or optionally substituted β-naphthyl group.

$R_1$ stands for a $C_1$–$C_6$ alkyl group such as methyl, ethyl, propyl, isopropyl, butyl, s-butyl, t-butyl, i-butyl, pentyl, neopentyl, isoamyl, and hexyl, $C_2$–$C_6$ alkenyl groups such as vinyl, propenyl, isopropenyl, and butenyl, $C_2$–$C_6$ alkynyl groups Such as ethynyl and propagyl, a $C_1$–$C_6$ haloalkyl group such as trifluoromethyl, difluoromethyl, chloromethyl, trichloromethyl, dichloromethyl and bromomethyl, or a $C_1$–$C_6$ haloalkenyl groups such as chloropropenyl, fluoropropenyl and chlorobutenyl.

Z stands for —$CR_2R_3$—, —$CH_2D$—, or —CH=CH—, $R_2$ and $R_3$ independently stand for hydrogen atom, a halogen atom such as fluorine, chlorine, bromino, and iodine, a $C_1$–$C_6$ alkyl group such as methyl, ethyl, propyl, isopropyl, butyl and hexyl, a $C_1$–$C_6$ alkoxy group such as methoxy, ethoxy, propoxy, isopropoxy, butoxy, t-butoxy, and hexyloxy, a $C_1$–$C_6$ haloalkyl group such as chloromethyl, fluoromethyl, dichloromethyl, difluoromethyl, trichloromethyl, trifluoromethyl, trichloroethyl, and trifluoromethyl, perfluoroethyl, perfloropropyl, and a $C_1$–$C_6$ alkylcarbon-yloxy group such as methylcarbonyloxy, ethylcarbonyloxy, propylcarbonyloxy, isopropylcarbonyloxy, butylcarbonyloxy and hexylcarbonyloxy, a $C_1$–$C_6$ alkylamino group such as methylamino, ethylamino, propylamino, isopropylamino, butylamino and t-butylamino. $S(O)pR_4$ (wherein p stands for an integer of 0 to 2 and $R_4$ stands for a $C_1$–$C_6$ alkyl group such as methyl, ethyl, propyl, isopropyl, and butyl), or $R_2$ and $R_3$ jointly stand for hydroxyimino group, a $C_1$–$C_6$ alkoxyimino group, =O, =$CH_2$, or =$NNHR_5$ (wherein $R_5$ stands for a $C_1$–$C_6$ alkoxycarbonyl group such as methoxycarbonyl, ethoxycarbonyl, propoxycarbonyl, isopropoxycarbonyl and butoxycarbonyl). D stands for $CH_2$, CO, O, or S, m stands for an integer from 0 to, providing that the plurality of $X_2$'s may be identical with or different from each other where m is 2 or more, and n stands for an integer from 0 to 5, providing that the plurality of Y's may be identical with or different from each other where n is 2 or more] or a salt thereof and a pesticide.

In this invention, as concrete examples or the substituent in the phenyl group optionally containing a substituent, the phenylmethyl group optionally containing a substituent, the phenoxy group optionally containing a substituent, the pyridyloxy group optionally containing a substituent, the pyridylthio group optionally containing a substituent, the phenylcarbonyloxy group optionally containing a substituent, the phenylcarbonylthio group optionally containing a substituent, and the naphthyl group optionally containing a substituent which are represented by Y, a halogen atom, a $C_1$–$C_6$ alkyl group, a $C_1$–$C_6$ haloalkyl group, a $C_1$–$C_8$ alkoxy group, a $C_1$–$C_6$ haloalkoxy group, a $C_1$–$C_6$ alkylthio group, a $C_1$–$C_6$ alkylamino group, nitro group, cyano group, hydroxy group, a $C_1$–$C_6$ alkylcarbonyloxy group, a $C_1$–$C_6$ alkoxy-carbonyl group, a phenyl group optionally containing such substituents as halogen atoms, $C_1$–$C_6$ alkyl groups, and $C_1$–$C_6$ alkyl groups, and $C_1$–$C_6$ haloalkyl groups, phenylthio groups optionally containing such substituents as halogen atoms, $C_1$–$C_6$ alkyl groups, and $C_1$–$C_6$ haloalkyl groups, phenylmethyl groups optionally containing such substituents as halogen atoms, $C_1$–$C_6$ alkyl groups, and $C_1$–$C_6$ haloalkyl groups, and pyridyloxy groups optionally containing such substituents as halogen atoms, $C_1$–$C_6$ alkyl groups, and $C_1$–$C_6$ haloalkyl groups may be cited. The phenyl groups and pyridyl groups may contain a plurality of diverse substituents.

Production of Compounds

The compounds according to this invention can be produced, for example, by the following methods.

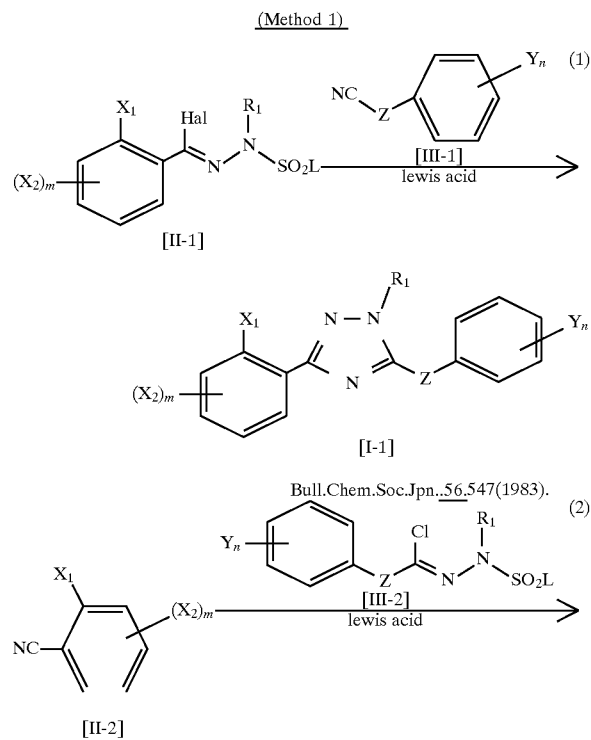

-continued (Method 1)

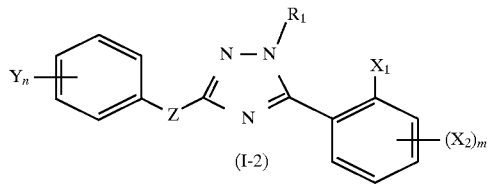
(I-2)

(wherein $X_1$, $X_2$, Y, $R_1$, Z, m and n have the same meanings as defined above, Hal stands for a halogen atom, and L stands for a $C_1$–$C_6$ alkyl group or a phenyl group optionally substituted with a $C_1$–$C_6$ alkyl group)

The reaction is carried out in the absence of a solvent or in an inert solvent such as benzene, toluene, xylene, dichlorobenzene, chloroform, dichloromethane, N,N-dimethylformamide, acetonitrile, dioxane, tetrahydrofuran, or dimethyl sulfoxide in the presence of a Lewis acid such as anhydrous aluminum chloride, titanium tetrachloride, or boron trifluoride ethyl ether complex compound at a temperature from 0° C. to the boiling point of the solvent for from several minutes to several dozen of hours.

(Method 2)

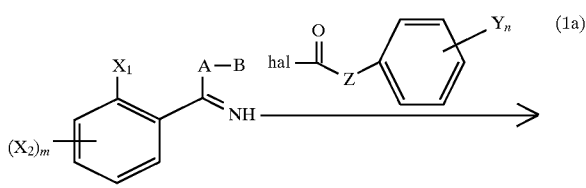
(1a)

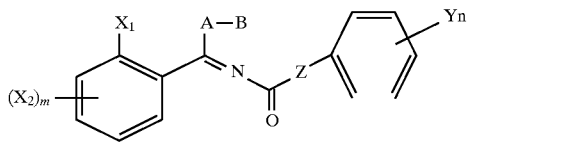
(IV-1)

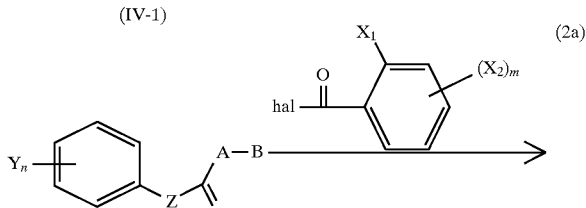
(2a)

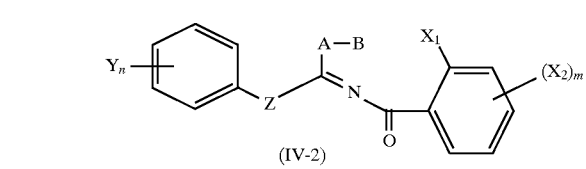
(IV-2)

(wherein $X_1$, $X_2$, Y, Z, m, and n have the same meanings as defined above, A stands for an oxygen atom or a sulfur atom, B stands for a $C_1$–$C_6$ alkyl group, and hal stands for a halogen atom).

The reaction is carried out in the absence of a solvent or in an inert solvent such as benzene, toluene, xylene, dichloro-benzene, chloroform, dichloromethane, N,N-dimethylformamide, acetonitrile, dioxane, tetrahydrofuran, or dimethyl sulfoxide, optionally in the presence or a base such as sodium hydride, sodium hydroxide, sodium carbonate, triethyl amine, or pyridine at a temperature from −20° C. to the boiling point of the solvent for from several minutes to several dozen of hours.

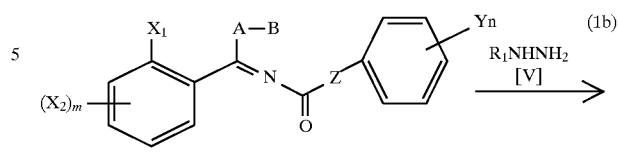
(1b)
[IV-1]

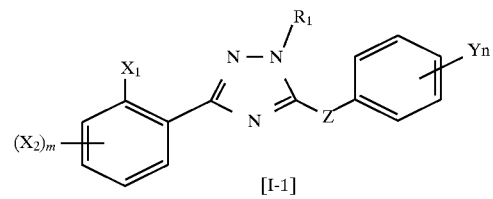
[I-1]

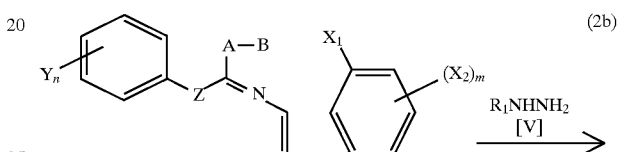
(2b)
[IV-2]

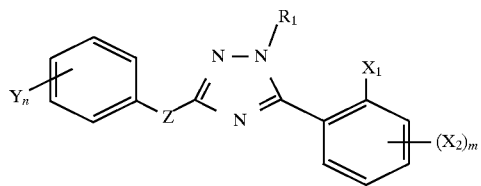

(wherein A, B, $X_1$, $X_2$, Y, $R_1$, Z, m, and n have the same meanings as defined above).

The reaction is carried out in the absence of a solvent or in an inert solvent such as benzene, toluene, xylene, dichloro-benzene, chloroform, dichloromethane, N,N-dimethylformamide, acetonitrile, dioxane, tetrahydrofuran, dimethyl sulfoxide, methyl alcohol, or ethyl alcohol at a temperature from 0° C. to the boiling point of the solvent for from several minutes to several dozen of hours.

(Method 3)

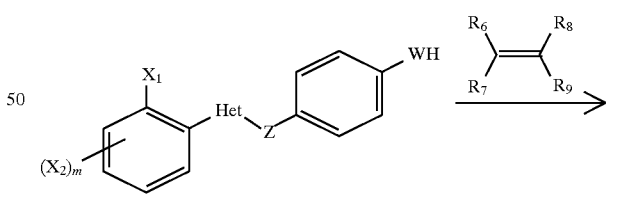

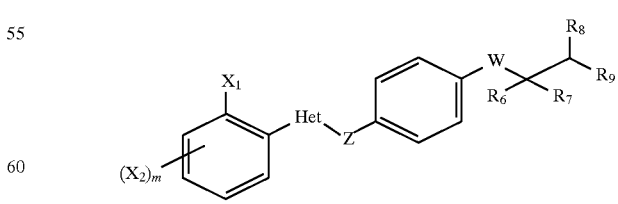

(wherein $X_1$, $X_2$, $R_1$, Z, and m have the same meanings as defined above, $R_6$, $R_7$, $R_8$, and $R_9$, equally or unequally stand for an alkyl group optionally substituted with hydrogen or an optionally substituted phenyl group, and Z stands for an oxygen atom, a sulfur atom, or a —NH group).

The reaction is carried out in an organic solvent in the presence of a catalyst, when necessary, at a temperature from −100° C. to the boiling point of the solvent from one hour to several dozen of hours. The solvents which can be effectively usable herein include dichloromethane, DMF, acetonitrile. THF, and chloroform, for example. The catalysts which can be effectively usable herein include trifluoromethane sulfonic acid, p-toluene sulfonic acid, sulfuric acid, and hydrochloric acid, fur example.

(Method 4)

The compound of this invention, depending on the kind of a substituent contained therein, can be produced by the reaction of the following formula or by suitably selecting a reaction similar to a known method.

-continued

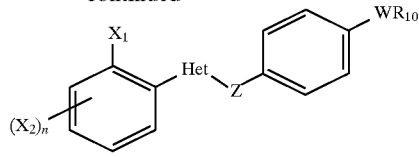

(wherein $X_1$, $X_2$, Y, $R_1$, Z, m, n, and Het have the same meanings as defined above, 1 stands for an eliminating group such as a halogen atom, and $R_{10}$ stands for an optionally substituted $C_1$–$C_6$ alkyl group, an optionally substituted phenyl group, or an optionally substituted pyridyl group).

a)

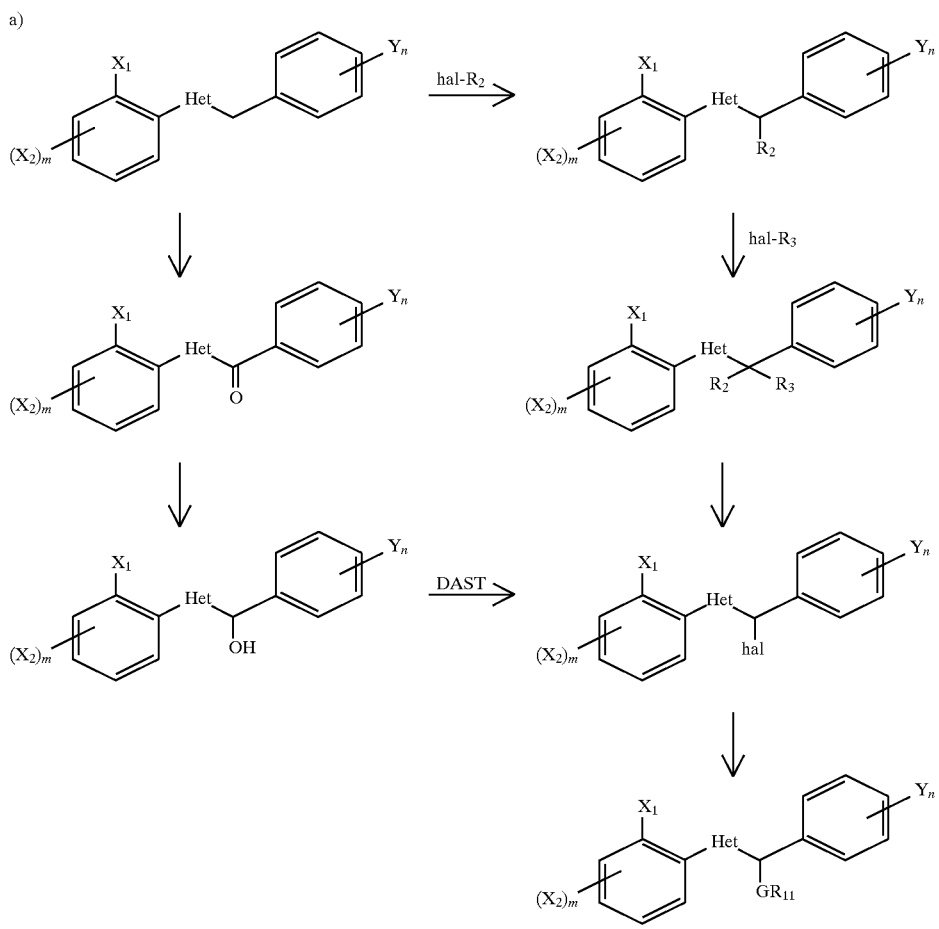

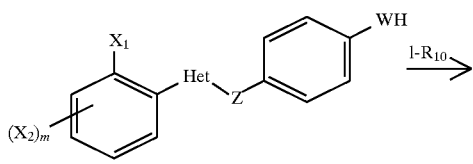

(wherein G stands for an oxygen atom, a sulfur atom, or —$NR_2$, $R_1$ and $R_2$ independently stand for an optionally substituted alkyl group, hal stands for a halogen atom, and DAST is an acronym of diethylaminosulfurt rifluoride, $R_3$ stands for an optionally substituted alkyl group).

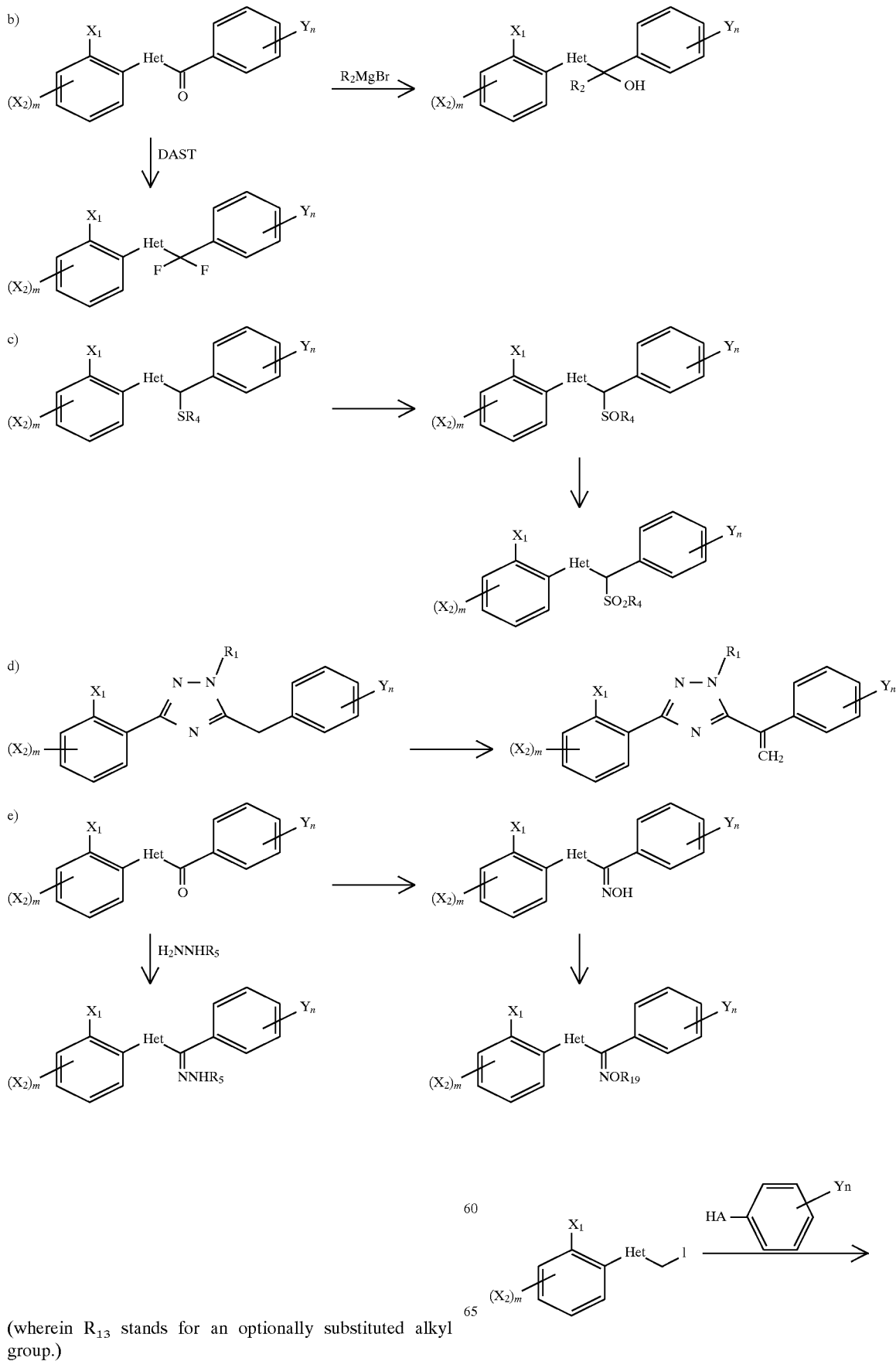
(wherein $R_{13}$ stands for an optionally substituted alkyl group.)

-continued

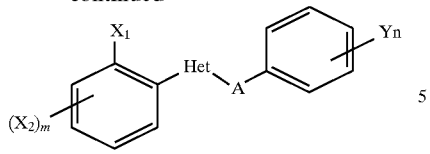

(wherein 1 stands for an eliminating group such as a halogen atom and A stands for an oxygen atom or a sulfur atom.)

As concrete examples of the salt of the triazole compound of this invention, inorganic salts such as hydrochlorides and organic salts such as citrates may be cited. These salts can be produced by a method in popular use.

Whichever of the methods mentioned above may be performed, the product aimed at can be obtained by subjecting the resultant reaction solution to a standard after-treatment.

The structure of the compound of this invention is identified by IR, NMR, Mass, etc.

EXAMPLES

Example 1 (Compound No. 2)

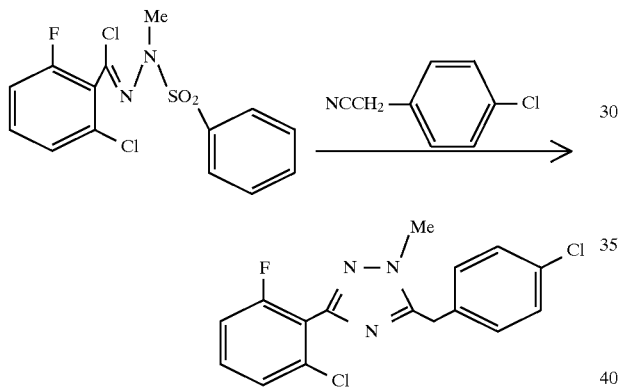

To a solution of 1.0 g of N-methyl-N-phenylsulfonyl-2-chloro-6-fluorobonzohydrazonoyl chloride in 10 ml of o-dichlorobenzene at room temperature, were added 0.43 g of p-chlorobenzyl cyanide and 0.41 g of anhydrous aluminum chloride. The reaction mixture was heated at 140° C. for 2 hours. After cooling, the reaction mixture was poured into iced water and extracted with ethyl acetate. The ethyl acetate layer was washed with water, dried over magnesium sulfate and concentrated under reduced pressure. The residue was subjected to silica gel chromatography to afford 0.7 g of 6-(4-chlorobenzyl)-3-(2-chloro-6-fluorophenyl)-1 methyl-1H-1,2,4-triazole. m.p.78.5°–80.5° C.

Example 2 (Compound No. 105)

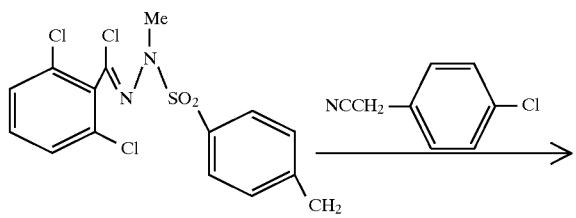

-continued

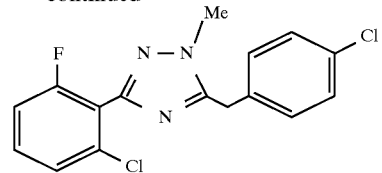

To a solution of 1.0 g of N-methyl-N-(p-toluenesulfonyl)-2,6-dichlorobenzohydrazonoyl chloride in 10 ml of o-dichlorobenzene at room temperature, were added 0.46 g of p-chlorobenzyl cyanide and 0.41 g of anhydrous aluminum chloride. The reaction mixture was heated at 120° C. for 30 minutes. Aster cooling, the section mixture was poured into iced-water and extracted with ethyl acetate. The ethyl acetate layer was washed with water, dried over magnesium sulfate and concentrated under reduced pressure. The residue was subjected to silica gel chromatography to afford 0.7 g of 5-(4-chlorobenzyl)-3 (2,6-dichlorophenyl)-1-methyl-1H-1,2,4-triazole. m.p.112°–115° C.

Example 3 (Compound No. 80)

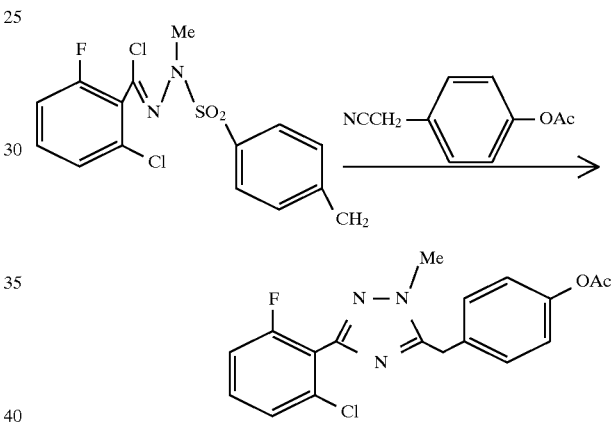

To a solution of 1.0 g of N-methyl-N-(p-toluenesulfonyl)-2-chloro-6-fluorobonzohydrazonoyl chloride in 10 ml of o-dichlorobenzene at room temperature, were added 0.56 g of p-acetoxybenzyl cyanide and 0.36 g of anhydrous aluminium chloride. The reaction mixture was heated at 120° C. for 30 minutes. After cooling, the rection mixture was poured into iced-water and extracted with ethyl acetate. The ethlyl acetate layer was washed with water, dried over magnesium sulfate and concentrated under reduced pressure.

The residue was subjected to silica gel chromatography to afford 0.7 g of 5-(4-acetoxybenzyl)-3-(2-chloro-6-fluorophenyl)-1-methyl-1H 1,2,4-triazole.

Example 4 (Compound No. 79)

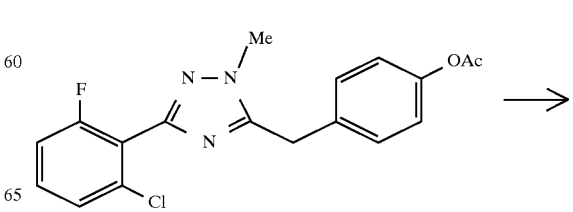

-continued

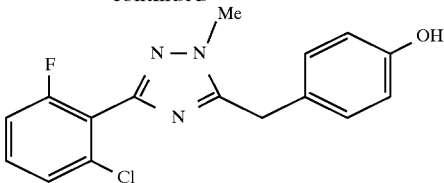

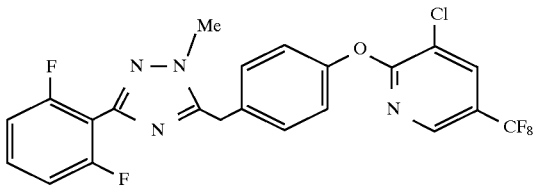

To a solution of 0.7 g of 5-(4-acetoxybenzyl)-3-(2-chloro-6-fluorophenyl)-1-methyl-1H-1,2,4-triazole in 10 ml of ethyl alcohol under ice-cooling, was added a solution of 0.62 g of potassium carbonate in 5 ml of water, and the reaction mixture was stirred at room temperature for 30 minutes, and then concentrated under reduced pressure. The residue was adjusted to pH 4 with diluted hydrochloric acid and extracted with ethyl acetate. The ethyl acetate layer was washed with water, dried over magnesium sulfate and concentrated under reduced pressure. The residue was subjected to silica gel chromatography to afford 0.6 g of 5-(4-hydroxybenzyl)-3-(2-chloro-6-fluorophenyl)-1-methyl-1H-1,2,4-triazole.

Example 5 (Compound No. 33)

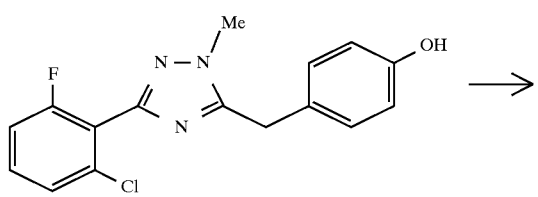

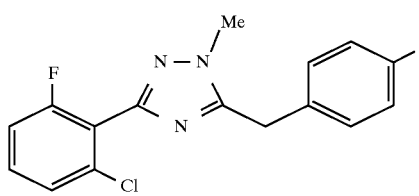

To a solution of 0.6 g of 5-(4-hydroxybenzyl)-3-(2-chloro-6-fluorophenyl)-1-methyl-1H-1,2,4-triazole in 10 ml of dichloromethane at −70° C. was added 0.29 g of trifluoromethanesulfonic acid and 2.1 g of isobutene was bubbled in a few minutes. After 1 hour of stirring at the same temperature, triethyamine was added to the solution and then the reaction mixture was warmed gradually to room temperature. The reaction mixture was poured into iced water and the organic layer was washed with water, dried over magnesium sulfate and concentrated under reduced pressure. The residue was subjected to silica gel chromatography to afford 0.55 g of 5-(4-t-butoxybenzyl)-3-(2-chloro-6-fluorophenyl)-1-methyl-1H-1,2,4-triazole. nD22.8 1.5458

Example 6 (Compound No. 101)

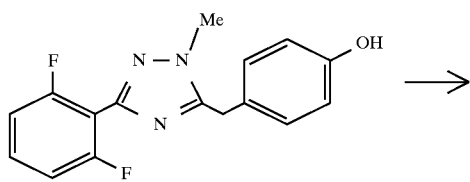

To a solution of 0.8 g of 5-(4-hydroxybenzyl)-3-(2,6-difluorophenyl)-1-methyl 1H-1,2,4-triazole in 10 ml of DMF at room temperature were added 0.4 g of anhydrous potassium carbonate and 0.63 g of 2,3-dichloro-5-trifluoromethylpyridine and then the suspension solution was heated to 70° C. or 1 hour. After cooling, the reaction mixture was poured into iced water and extracted with ethyl acetate. The ethyl acetate layer was washed with water, dried over magnesium sulfate and concentrated under reduced pressure. The residue was subjected to silica gel chromatography to afford 0.55 g of 5-(4-(3-chloro-5-trifluoromethylpyridin-2-yloxy)-benzyl)-3-(2,6-difluorophenyl)-1-methyl-1H-1,2,4-triazole.

nD25.5 1.5541

Example 7 (Compound No. 7)

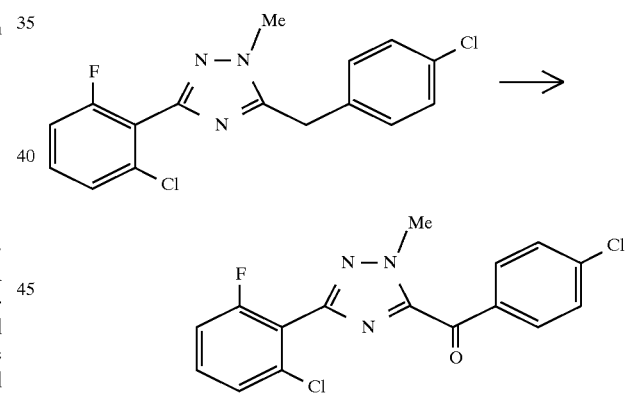

To a solution of 2.0 g of 5-(4-chlorobenzyl)-3-(2-chloro-6-fluorophenyl)-1-methyl-1H-1,2,4-triazole in 20 ml of acetic acid at 10° C., was added 1.2 g of chromic anhydride. After stirring at room temperature overnight, the reaction mixture was poured into iced water and extracted with ethyl acetate. The ethyl acetate layer was washed with a saturatedaqueous sodium hydrogen carbonate solution and then with water, dried over magnesium sulfate and concentrated under reduced pressure. The residue was subjected to silica gel chromatography to afford 1.7 g of 5-(4-chlorobenzoyl)-3-(2-chloro-6-fluorophenyl)-1-methyl-1H-1,2,4-triazole.

m.p.108°–111° C.

Example 8 (Compound No. 3)

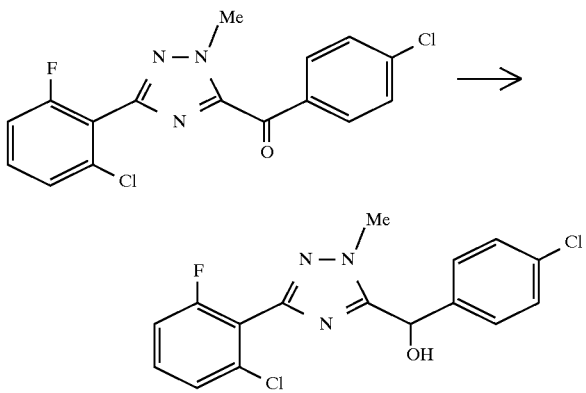

To a solution of 1.1 g of 5-(4-chlorobenzyl)-3-(2-chloro-6-fluorophenyl)-1-methyl-1H-1,2,4-triazole in 15 ml of ethyl alcohol at 0° C. was added potionwise 0.06 g of sodium borohrdride. After 30 minutes, the rection mixture was poured into iced water and extracted with chloroform, the chloroform solution was washed with water, dried over magnesium sulfate and concentrated under reduced pressure. The residue was washed with n-hexane to afford 1.0 g of 5-(4-chloro-α-hydroxybenzyl)-3-(2-chloro-6-fluorophenyl)-1-methyl-1H-1,2,4-triazole.

m.p.141°–143° C.

Example 9 (Compound No. 6)

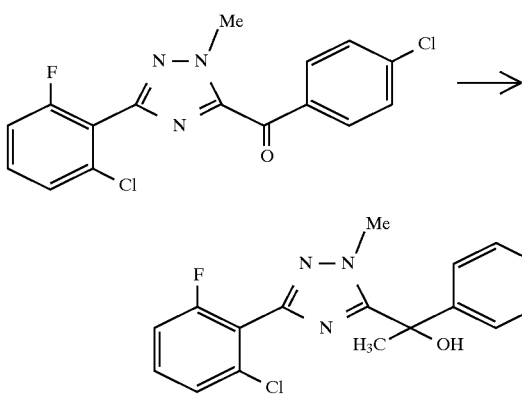

Under an atmosphere of nitrogen, to a solution of 1.5 of 5-(4-chlorobenzoyl)-3-(2-chloro-6-fluorophenyl)-1-methyl-1H 1,2,4-triazole in diethl ether at −70° C. was added dropwise 12 ml of methylmagnesium bromide. After 1 hour, the reaction mixture was warmed to room temperature stirred overnight, Then 36 ml of a 2N aqueous solution of sulfuric acid was added to the solution under iced-cooling, the mixture was poured into iced water and extracted with ethyl acetate. The ethyl acetate layer was washed with water, dried over magnesium sulfate and concentrated under reduced pressure. The residue was subjected to silica gelchromatography to afford 1.3 g of 5-(4-chloro-α-hydroxy-α-methylbenzyl)-3-(2-chloro-6-fluorophenyl)-1-methyl 1H-1,2,4-triazole. mp.198°–200° C.

Example 10 (Compound No. 4)

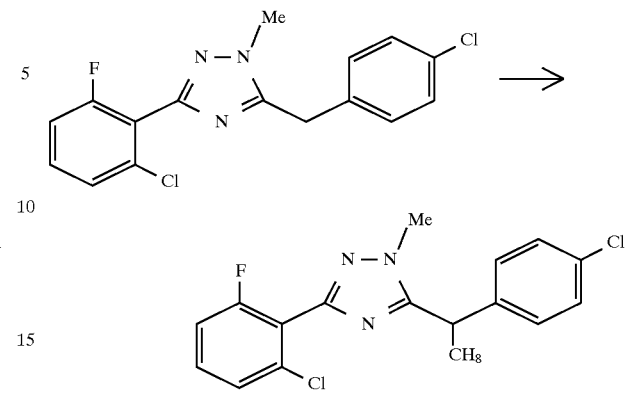

To a solution of 1.0 g of 5-(4 chlorobenzyl)-3-(2-chloro-6-fluorophenyl)-1-methyl-1H-1,2,4-triazole in 10 ml of N,N-dimethylformamide at 0° C. was added 0.13 g of 60% sodiumhydride. After stirring at room temperature for 30 minutes, 0.42 g of methyl iodide added dropwise to the solution at 0° C. The reaction mixture was stirred at the same temperature for 1 hour and then at room temperature for 2 hours, poured into iced water and extracted with ethyl acetate. The ethyl acetate layer was washed with water, dried over magnesium sulfate and concentrated under reduced pressure. The residue was subjected to silica gel chromatography to afford 1.0 g of 5-(4-chloro-α-methylbenzyl)-3-(2-chloro-6-fluorophenyl)-1-methyl-1H-1,2,4-triazole.

nD24.7 1.5774

Example 11 (Compound No. 8)

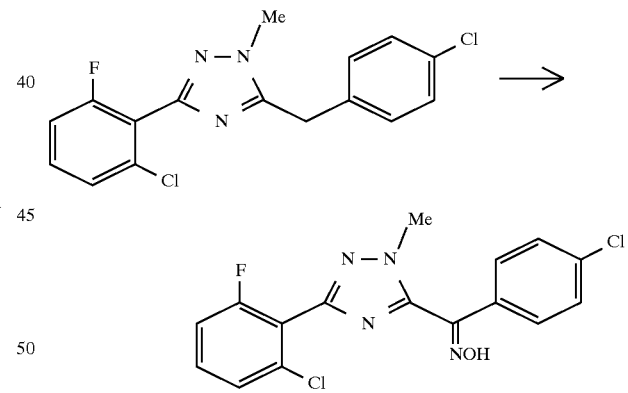

To a solution of 0.9 g of 5-(4-chlorobenzyl)-3-(2-chloro-6-fluorophenyl)-1-methyl-1H-1,2,4-triazole in 10 ml of benzene, was added 0.8 g of potassium t-butoxide at room temperature. After 3 hours of stirring at the same temperature, 0.84 g of iso-amyl nitrate was added to the solution, followed by stirring overnight. The rotation mixture was poured into iced water and extracted with ethyl acetate. The ethyl acetate layer was washed with water, dried over magnesium sulfate, filtered and concentrated under reduced pressure to afford 0.3 g of 5-(4-chloro-α,α-hydroxyiminobenzyl)-3-(2-chloro 6-fluorophenyl)-1-methyl-1H-1,2,4l-triazole.

m.p.195°–198° C.

Example 12 (Compound No. 193)

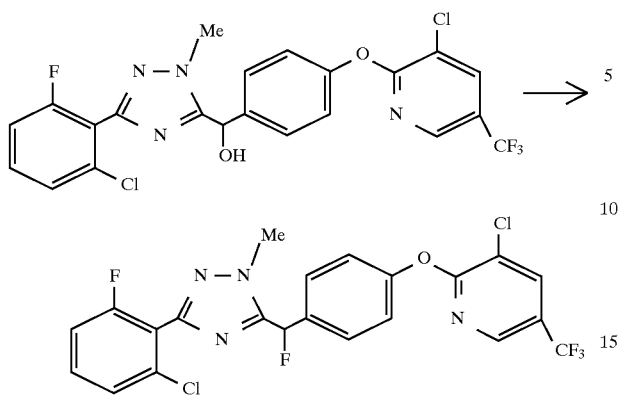

To a solution of 0.9 g of 5-{4-(3-chloro-5-trifluoromethylpyridin-2-yloxy)-α-hydroxybenzyl}-3-(2-chloro-6-fluorophenyl)-1-methyl-1H-1,2,4-triazole in 10 ml of benzene at room temperature, were added 0.85 g of diethylaminosulfur trifluoride (DAST). After stirring at room temperature for 1 hour, the reaction mixture was poured into iced water and extracted with ethyl acetate. The ethyl acetate layer was washed with a saturated aqueous sodium hydrogen carbonate and then with water, dried over magnesium sulfate and concentrated under reduced pressure. The residue was subjected to silica gel chromatography to afford 0.8 g of 5-{4-(3-chloro-5-trifluoromethylpyridin-2-yloxy)-α-fluorobenzyl}-3-(2-chloro-6-fluorophenyl)-1 methyl-1H-1,2,4-triazole.

nD25.5 1.5665

Example 13 (Compounds No. 209, 210)

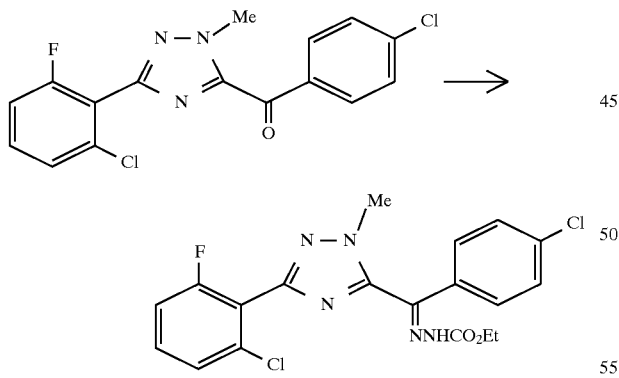

A solution of 1.5 g of 5-(4-chlorobenzoyl)-3-(2-chloro-6-fluorophenyl)-1-methyl-1H-1,2,4-triazole and 0.45 g of ethyl carbazate, a small amount of p-toluenesulfonic acid in 20 ml of toluene, was refluxed fo 3 hours. After concentrated under reduced pressure, the residue was subjected to silica gel chromatography to afford 0.8 g of 5-(4-chloro-α,α-ethoxycarbonylhydrazonobenzyl)-3-(2-chloro-6-fluorophenyl)-1-methyl-1H-1,2,4-triazole(m.p.134°–136° C.), and 0.4 g of the isomer (m.p.154°–156° C.).

Example 14 (Compound No. 233)

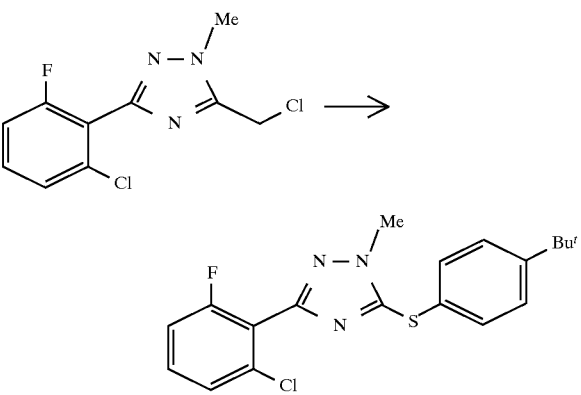

To a solution of 0.51 g of 4-t-butylthiophenol in 10 of DMF at 0° C. was added portionwise 0.14 g of 60% sodium hydride, and stirred at room temperature overnight. 0.8 g of 5-chloromethyl-3-(2-chloro-6-fluorophenyl1)-1-methyl-1H-1,2,4-triazole was added to the solution at 0° C., and stirred at room temperature overnight. The reaction mixture was poured into iced-water and extracted with ethyl acetate. The ethyl acetate layer was washed with water, dried over magnesium sulfate and concentrated under reduced pressure. The residue was subjected to silica gel chromatography to afford 1.0 g of 5-(4-t-butylphenythiometh yl)-3-(2-chloro 6-fluorophenyl)-1-methyl-1H-1,2,4-triazole. nD24.5 1.5579

Example 15 (Compound No. 235)

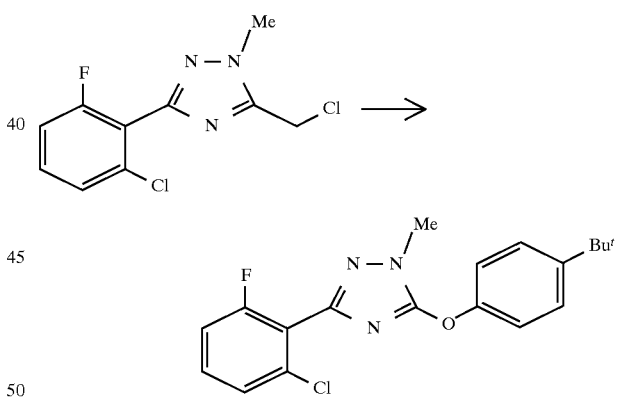

To a solution of 0.6 g or 4-t-butylphenol in 10 ml of DMF at 0° C., was added portionwise 0.13 g of 60% sodium hydride, and stirred at room temperature for 1 hour. 1.0 g of 5-chloromethyl-3-(2-chloro-6-fluorophenyl)-1-methyl-1H-1,2,4 triazole was added to the solution at 0° C., and stirred at room temperature overnight. The reaction mixture was poured into iced water and extracted with ethyl acetate. The ethyl acetate layer was washed with water, dried over magnesium sulfate and concentrated under reduced pressure. The residue was subjected to silica gel chromatography to afford 1.3 g of 5-(4-t-butylphenoxymethyl)-3-(2-chloro-6-fluorophenyl)-1-methyl-1H-1,2,4-triazole. m.p.84°–86° C.

Example 16 (Compound No. 5)

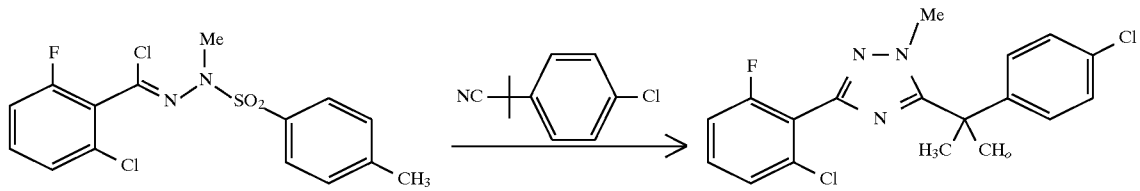

To a solution of 2.0 g of N-methyl-N-(p-toluenesulfonyl)-2-chloro-6-fluorobonzohydrazonoyl chloride in 20 ml of o-dichlorobenzene at room temperature, were added 1.1 g of 4-chloro-α,α-dimethylbenzyl cyanide and 0.85 g of anhydrous aluminum chloride, and the reaction mixture was heated at 120° C. or 30 minutes. After cooling, the rection mixture was poured into iced water and extracted with ethyl acetate. The ethyl acetate layer was washed with water, dried over magnesium sulfate and concentrated under reduced pressure. The residue was subjected to silica gel chromatography to afford 1.5 g of 5-(4-chloro α,α-dimethylbenzyl)-3-(2-chloro-6-fluorophenyl)-1-methyl-1H-1,2,4-triazole.

nD22.2 1.5693

Example 17 (Product No. 298)

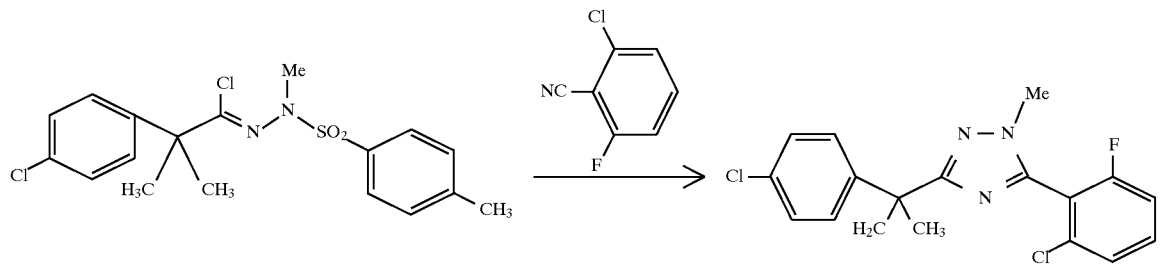

To a solution of 0.7 g of N-methyl-N-(p-toluenesulfonyl)-(α, α-dimethyl-4-chlorophenylacetohydrazonoyl chloride in 7 ml of o-dichlorobenzene at room temperature, were added 0.33 g of 2-chloro-6-fluorobenzonitrile and 0.28 g of anhydrous aluminium chloride, and the reaction mixture was heated at 120° C. for 30 minutes. After cooling, the reaction mixture was poured into iced water and extracted with ethyl acetate. The ethyl acetate layer was washed with water, dried over magnesium sulfate and concentrated under reduced pressure. The residue was subjected to silica gel chromatography to afford 0.6 g of 5-(2-chloro-6-fluorophenyl)-3-(4-chloro-α,α-dimethylbenzyl)-1-methyl-1H-1,2,4-triazole. m.p.97°–100° C.

Typical examples of the present invention, including the compounds produced in the preceding examples, are shown in Table 1.

TABLE 1
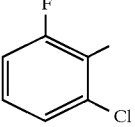
| Compound No. | $Q_1$ | $R_1$ | $Q_2$ | Physical const. Melting Point °C. Refractive Index |
|---|---|---|---|---|
| 1 | 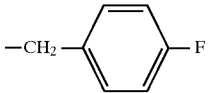 | Me | 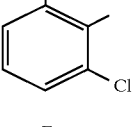 | 66.0–67.0 |
| 2 | 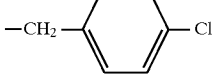 | Me | 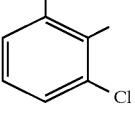 | 78.5–80.5 |
| 3 | 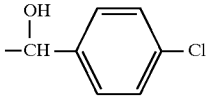 | Me | 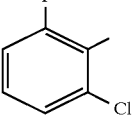 | 141–148 |
| 4 | 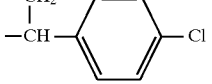 | Me | 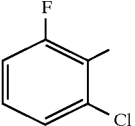 | $n_D^{84.7}$ 1.5774 |
| 5 |  | Me | 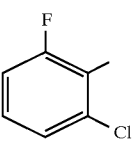 | $n_D^{22.2}$ 1.5693 |
| 6 |  | Me | 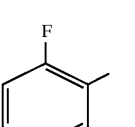 | 198–200 |
| 7 | 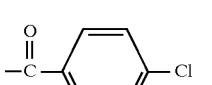 | Me | 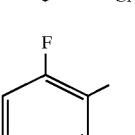 | 108–111 |
| 8 | 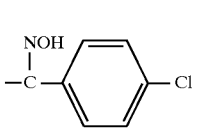 | Me | 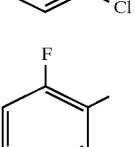 | 195–198 |
| 9 | 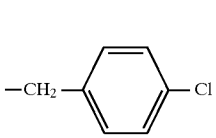 | Et | —CH$_2$—⟨4-Cl-C$_6$H$_4$⟩ | $n_D^{88.0}$ 1.5750 |

TABLE 1-continued
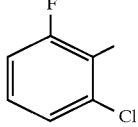
| Compound No. | $Q_1$ | $R_1$ | $Q_2$ | Physical const. Melting Point °C. Refractive Index |
|---|---|---|---|---|
| 10 | 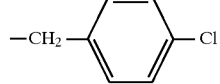 | $^i$Pr | 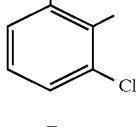 | |
| 11 | 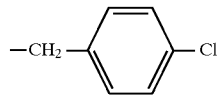 | $^n$Bu | 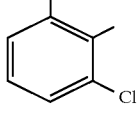 | $n_D^{87.4}$ 1.5577 |
| 12 | 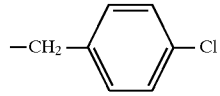 | FCH$_2$ | 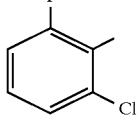 | |
| 13 | 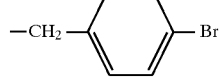 | Me | 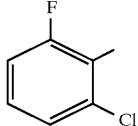 | |
| 14 | 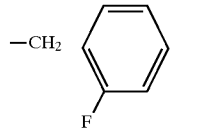 | Me | 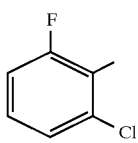 | 77–80 |
| 15 | 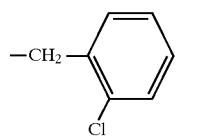 | Me | 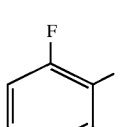 | 91–101 |
| 16 | 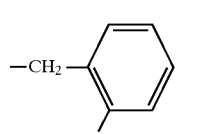 | Me | 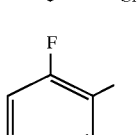 | |
| 17 | 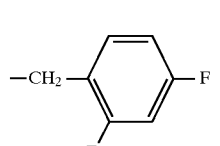 | Me | 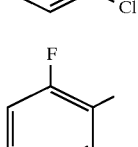 | $n_D^{98.0}$ 1.5544 |
| 18 | | Me | 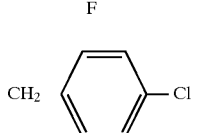 | 98–99 |

TABLE 1-continued
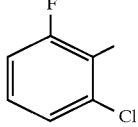
| Compound No. | $Q_1$ | $R_1$ | $Q_2$ | Physical const. Melting Point °C. Refractive Index |
|---|---|---|---|---|
| 19 | 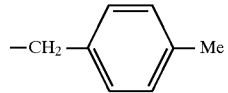 | Me | —CH$_2$—⟨C$_6$H$_4$⟩—Me | 117–118 |
| 20 | 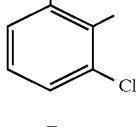 | Me | —CH$_2$—⟨C$_6$H$_4$⟩—$^i$Pr | 103–104 |
| 21 | 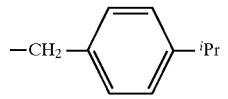 | Me | —CH$_2$—⟨C$_6$H$_4$⟩—$^t$Bu | 91–98 |
| 22 | 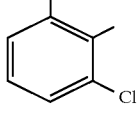 | Et | —CH$_2$—⟨C$_6$H$_4$⟩—$^t$Bu | |
| 23 |  | $^i$Pr | —CH$_2$—⟨C$_6$H$_4$⟩—$^t$Bu | |
| 24 | 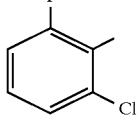 | Me | —C(=O)—⟨C$_6$H$_4$⟩—$^t$Bu | |
| 25 | 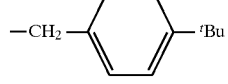 | Me | —CH(OH)—⟨C$_6$H$_4$⟩—$^t$Bu | |
| 26 | 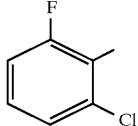 | Me | —CH(CH$_3$)—⟨C$_6$H$_4$⟩—$^t$Bu | |
| 27 | 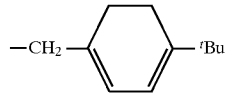 | Me | —CH$_2$—⟨C$_6$H$_3$(OBt)⟩—$^t$Bu | $n_D^{88.5}$ 1.6698 |

TABLE 1-continued
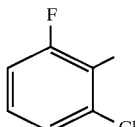
| Compound No. | $Q_1$ | $R_1$ | $Q_2$ | Physical const. Melting Point °C. Refractive Index |
|---|---|---|---|---|
| 28 | 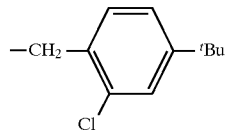 | Me | 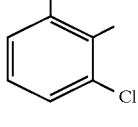 | |
| 29 | 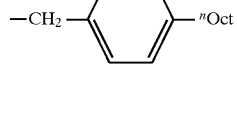 | Me | —CH$_2$—⟨C$_6$H$_4$⟩—$^n$Oct | |
| 30 | 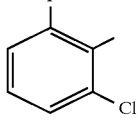 | Me | —CH$_2$—⟨C$_6$H$_4$⟩—CF$_3$ | |
| 31 | 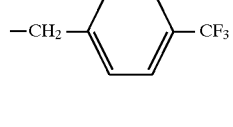 | Me | —CH$_2$—⟨C$_6$H$_4$⟩—OMe | $n_D^{24.0}$ 1.5755 |
| 32 | 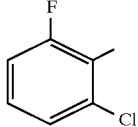 | Me | CH$_2$—⟨C$_6$H$_4$⟩—O$^i$Pr | |
| 33 | 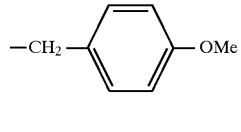 | Me | —CH$_2$—⟨C$_6$H$_4$⟩—O$^t$Bu | $n_D^{22.8}$ 1.5458 |
| 34 | 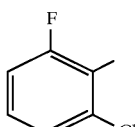 | Et | —CH$_2$—⟨C$_6$H$_4$⟩—O$^t$Bu | |
| 35 | 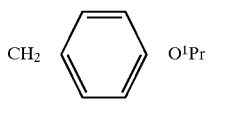 | $^i$Pr | —CH$_2$—⟨C$_6$H$_4$⟩—O$^t$Bu | |
| 36 | 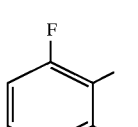 | Me | —C(=O)—⟨C$_6$H$_4$⟩—O$^t$Bu | |

TABLE 1-continued
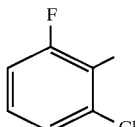
| Compound No. | Q₁ | R₁ | Q₂ | Physical const. Melting Point °C. Refractive Index |
|---|---|---|---|---|
| 37 | 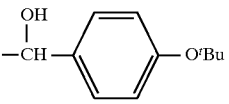 | Me | 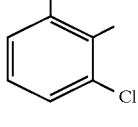 | |
| 38 |  | Me | 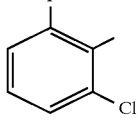 | |
| 39 | 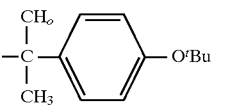 | Me | 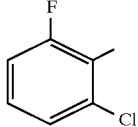 | |
| 40 | 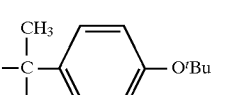 | Me | 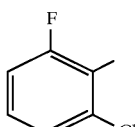 | |
| 41 | 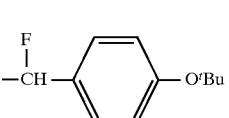 | Me | 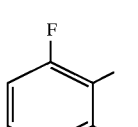 | |
| 42 | 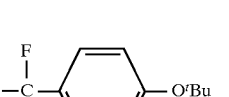 | Me | 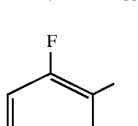 | |
| 43 |  | Me | 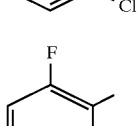 | |
| 44 |  | Me | 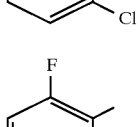 | |
| 45 | 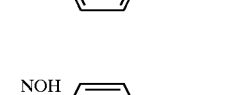 | Me | | |

TABLE 1-continued
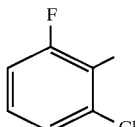
| Compound No. | $Q_1$ | $R_1$ | $Q_2$ | Physical const. Melting Point °C. Refractive Index |
|---|---|---|---|---|
| 46 |  | Me | 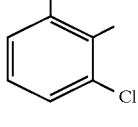 | |
| 47 | 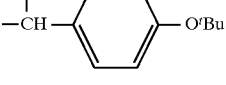 | Me | 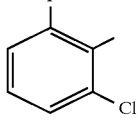 | |
| 48 | 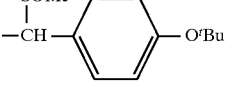 | Me | 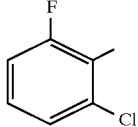 | |
| 49 | 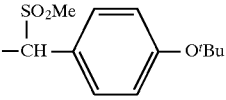 | Me | 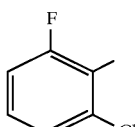 | |
| 50 | 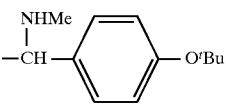 | Me | 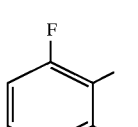 | |
| 51 | 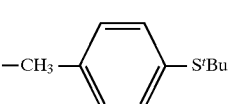 | Me | 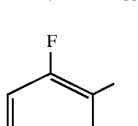 | |
| 52 | 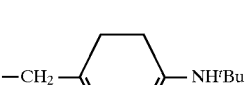 | Me | 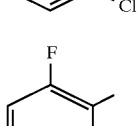 | |
| 53 | 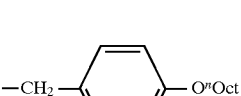 | Me | 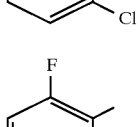 | $n_D^{20.0}$ 1.5396 |
| 54 |  | Me | | |

TABLE 1-continued
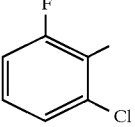
| Compound No. | Q₁ | R₁ | Q₂ | Physical const. Melting Point °C. Refractive Index |
|---|---|---|---|---|
| 55 |  | Me | —CH₂—⟨C₆H₄⟩—SMe | |
| 56 | 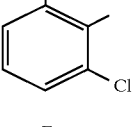 | Me | —CH₂—⟨C₆H₄⟩—NMe₂ | |
| 57 | 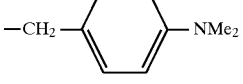 | Me | —CH₂—⟨C₆H₄⟩—NO₂ | |
| 58 | 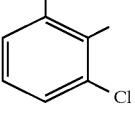 | Me | —CH₃—⟨C₆H₄⟩—CN | |
| 59 | 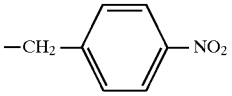 | Me | —CH₂—⟨C₆H₄⟩—CO₂Me | |
| 60 | 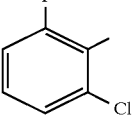 | Me | —CH₂—⟨C₆H₄⟩—O—⟨C₆H₅⟩ | $n_D^{28.5}$ 1.5968 |
| 61 |  | Me | —CH₂—⟨C₆H₄⟩—O—⟨C₆H₄⟩—CF₃ | |
| 62 | 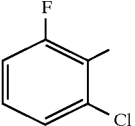 | Me | —CH₂—⟨C₆H₄⟩—O—⟨C₆H₄⟩—Me | |
| 63 | 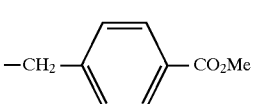 | Me | —CH₂—⟨C₆H₄⟩—O—⟨C₆H₄⟩—CF₃ | |

TABLE 1-continued
| Compound No. | Q₁ | R₁ | Q₂ | Physical const. Melting Point °C. Refractive Index |
|---|---|---|---|---|
| 64 | 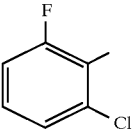 | Me | 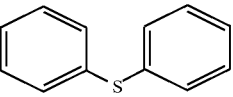 | |
| 65 | 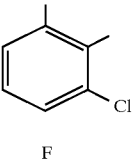 | Me | 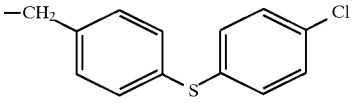 | |
| 66 | 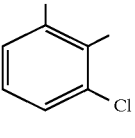 | Me | 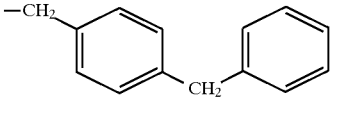 | |
| 67 | 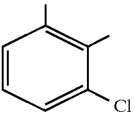 | Me | 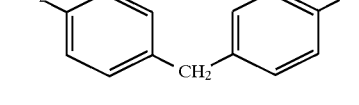 | |
| 68 | 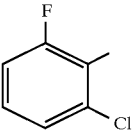 | Me | 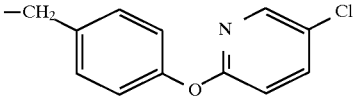 | |
| 69 | 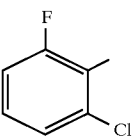 | Me | 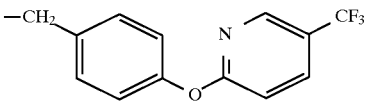 | |
| 70 | 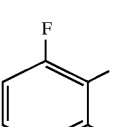 | Me | 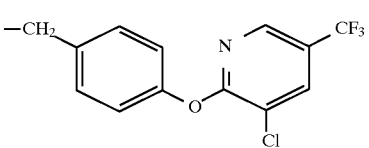 | $n_D^{22.5}$ 1.5603 |
| 71 | 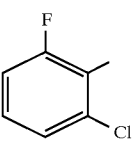 | Me | 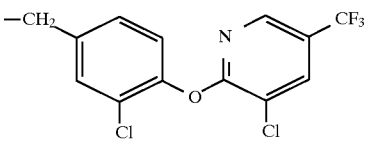 | |
| 72 | 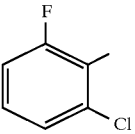 | Me | 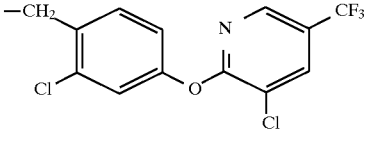 | |

TABLE 1-continued
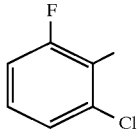
| Compound No. | Q₁ | R₁ | Q₂ | Physical const. Melting Point °C. Refractive Index |
|---|---|---|---|---|
| 73 | 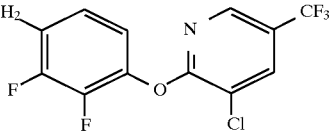 | Me | 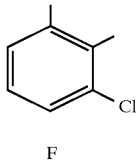 | |
| 74 | 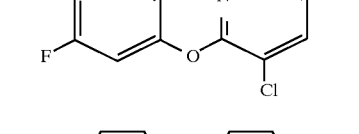 | Me | 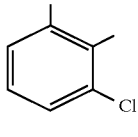 | |
| 75 | 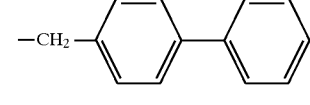 | Me | 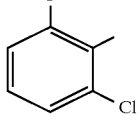 | 131–132.5 |
| 76 | 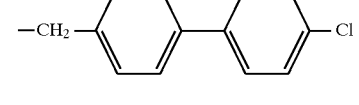 | Me | 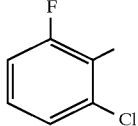 | 133–134.5 |
| 77 | 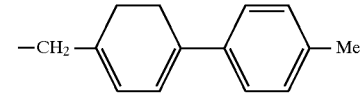 | Me | 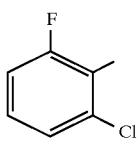 | |
| 78 | 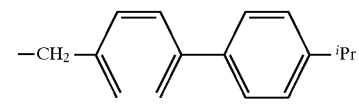 | Me | 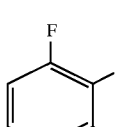 | |
| 79 | 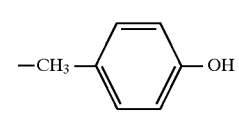 | Me | 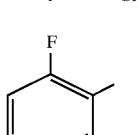 | Vis.Oil |
| 80 | 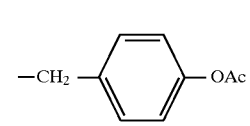 | Me | 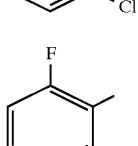 | Vis.Oil |
| 81 | 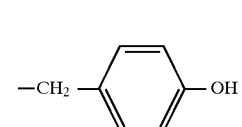 | Me | —CH₂—⌬—OH | Vis.Oil |

TABLE 1-continued
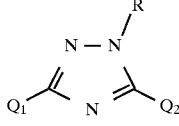
| Compound No. | Q₁ | R₁ | Q₂ | Physical const. Melting Point °C. Refractive Index |
|---|---|---|---|---|
| 82 | 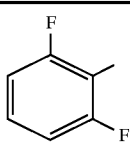 | Me | 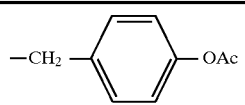 —CH₂—⟨⟩—OAc | $n_D^{24.0}$ 1.5518 |
| 83 | 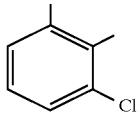 | Me | 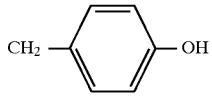 CH₂—⟨⟩—OH | |
| 84 | 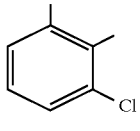 | Me | 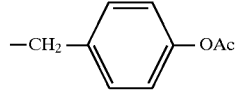 —CH₂—⟨⟩—OAc | |
| 85 | 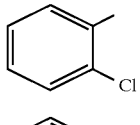 | Me | 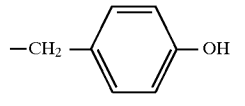 —CH₂—⟨⟩—OH | |
| 86 | 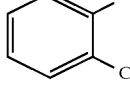 | Me | 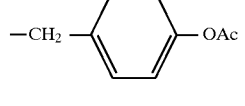 —CH₂—⟨⟩—OAc | |
| 87 | 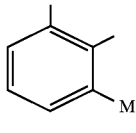 | Me | 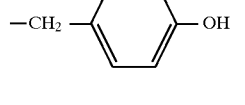 —CH₂—⟨⟩—OH | |
| 88 | 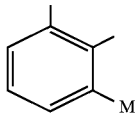 | Me | 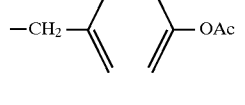 —CH₂—⟨⟩—OAc | |
| 89 | 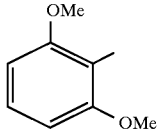 | Me | 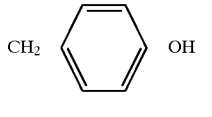 CH₂—⟨⟩—OH | |
| 90 | 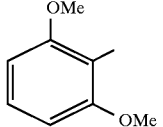 | Me | 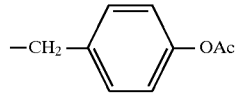 —CH₂—⟨⟩—OAc | |
| 91 | 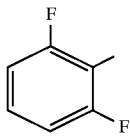 | Me | 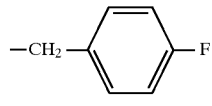 —CH₂—⟨⟩—F | $n_D^{23.0}$ 1.5561 |

TABLE 1-continued
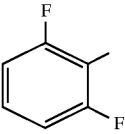
| Compound No. | Q₁ | R₁ | Q₂ | Physical const. Melting Point °C. Refractive Index |
|---|---|---|---|---|
| 92 | 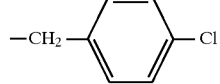 | Me | 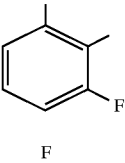 | 80–83 |
| 93 | 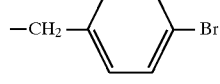 | Me | 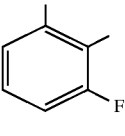 | |
| 94 | 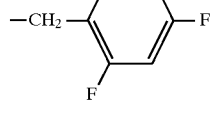 | Me | 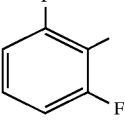 | |
| 95 | 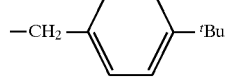 | Me | 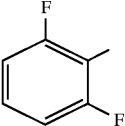 | 76–78 |
| 96 | 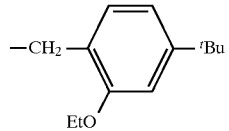 | Me | 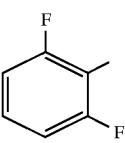 | $n_D^{24.4}$ 1.5422 |
| 97 | 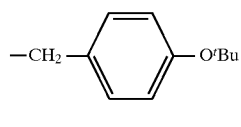 | Me | 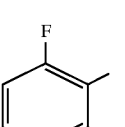 | 74–75 |
| 98 | 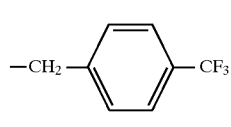 | Me | 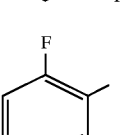 | |
| 99 | 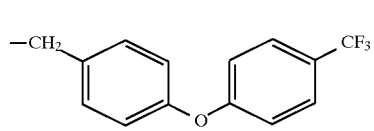 | Me | 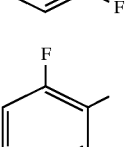 | |
| 100 | 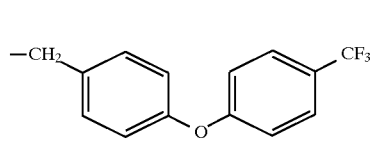 | Me | | |

TABLE 1-continued structure:
N—N(R)
Q1-C=N-C-Q2 (triazole core)

| Compound No. | Q1 | R1 | Q2 | Physical const. Melting Point °C. Refractive Index |
|---|---|---|---|---|
| 101 | 2,6-difluorophenyl | Me | -CH2-C6H4-O-(3-Cl,5-CF3-pyridin-2-yl) | $n_D^{25.5}$ 1.5541 |
| 102 | 2,6-difluorophenyl | Me | -CH2-C6H4-C6H4-Cl | |
| 103 | 2,6-difluorophenyl | Me | -CH3-C6H4-C6H4-iPr | |
| 104 | 2,6-dichlorophenyl | Me | -CH2-C6H4-F | 125–127 |
| 105 | 2,6-dichlorophenyl | Me | -CH2-C6H4-Cl | 112–115 |
| 106 | 2,6-dichlorophenyl | Me | -CH2-C6H4-Br | |
| 107 | 2,6-dichlorophenyl | Me | -CH2-C6H3(3,4-F2) | 131–133 |
| 108 | 2,6-dichlorophenyl | Me | -CH2-C6H4-tBu | $n_D^{28.0}$ 1.5711 |
| 109 | 2,6-dichlorophenyl | Me | -CH2-C6H3(3-OEt,4-tBu) | |

TABLE 1-continued
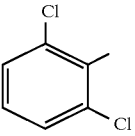
| Compound No. | $Q_1$ | $R_1$ | $Q_2$ | Physical const. Melting Point °C. Refractive Index |
|---|---|---|---|---|
| 110 |  | Me | 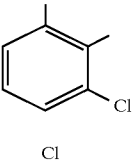 —CH₂—⟨⟩—O^tBu | 149–151 |
| 111 | 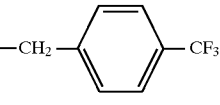 | Me | —CH₂—⟨⟩—CF₃ | |
| 112 | 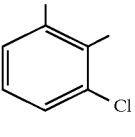 | Me | —CH₂—⟨⟩—O—⟨⟩—CF₃ | |
| 113 | 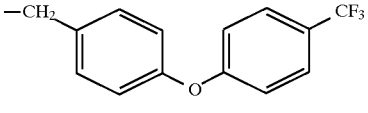 | Me | —CH₂—⟨⟩—O—⟨⟩—CF₃ | |
| 114 | 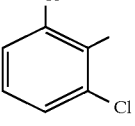 | Me | 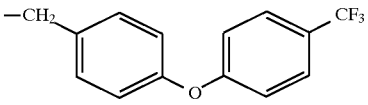 | 122–123 |
| 115 | 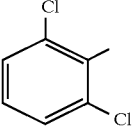 | Me | 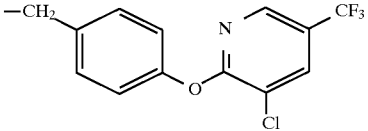 | |
| 116 | 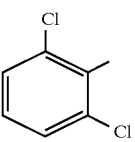 | Me | CH₂—⟨⟩—⟨⟩—^iPr | |
| 117 | 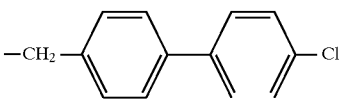 | Me | —CH₂—⟨⟩—F | |
| 118 | 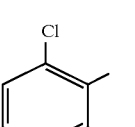 | Me | —CH₂—⟨⟩—Cl | |

TABLE 1-continued
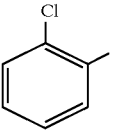
| Compound No. | $Q_1$ | $R_1$ | $Q_2$ | Physical const. Melting Point °C. Refractive Index |
|---|---|---|---|---|
| 119 | 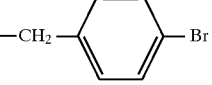 2-Cl-C6H4 | Me | —CH2—C6H4—4-Br | |
| 120 | 2-Cl-C6H4 | Me | —CH2—(2,4-F2-C6H3) | |
| 121 | 2-Cl-C6H4 | Me | —CH2—C6H4—4-$^t$Bu | |
| 122 | 2-Cl-C6H4 | Me | —CH2—(3-EtO-4-$^t$Bu-C6H3) | |
| 123 | 2-Cl-C6H4 | Me | —CH2—C6H4—4-O$^t$Bu | |
| 124 | 2-Cl-C6H4 | Me | —CH2—C6H4—4-CF3 | |
| 125 | 2-Cl-C6H4 | Me | —CH2—C6H4—4-O—C6H4—4-CF3 | |
| 126 | 2-Cl-C6H4 | Me | —CH2—C6H4—4-O—C6H4—4-CF3 | |
| 127 | 2-Cl-C6H4 | Me | —CH2—C6H4—4-O—(3-Cl-5-CF3-pyridin-2-yl) | |

TABLE 1-continued

Structure: Q₁-C(=N-N(R)-N=)-Q₂ (1,2,4-triazole with R on N)

| Compound No. | Q₁ | R₁ | Q₂ | Physical const. Melting Point °C. Refractive Index |
|---|---|---|---|---|
| 128 | 2-Cl-C₆H₄ | Me | —CH₂—(4,4'-biphenyl)—Cl | |
| 129 | 2-Cl-C₆H₄ | Me | —CH₃—(4,4'-biphenyl)—ⁱPr | |
| 130 | 2,3-diMe-C₆H₃ | Me | CH₂—C₆H₅—P | |
| 131 | 2,3-diMe-C₆H₃ | Me | —CH₂—C₆H₄—4-Cl | |
| 132 | 2,3-diMe-C₆H₃ | Me | —CH₂—C₆H₄—4-Br | |
| 133 | 2,3-diMe-C₆H₃ | Me | —CH₂—C₆H₃—2,4-F₂ | |
| 134 | 2,3-diMe-C₆H₃ | Me | —CH₃—C₆H₄—4-ᵗBu | |
| 135 | 2,3-diMe-C₆H₃ | Me | —CH₂—C₆H₃(3-OEt)(5-ᵗBu) | |
| 136 | 2,3-diMe-C₆H₃ | Me | —CH₂—C₆H₄—4-OᵗBu | |

TABLE 1-continued

Structure:
$$Q_1-C(=N-N(R)-N=)-C-Q_2$$ (1,2,4-triazole with R on N, Q1 and Q2 at 3,5-positions)

| Compound No. | Q₁ | R₁ | Q₂ | Physical const. Melting Point °C. Refractive Index |
|---|---|---|---|---|
| 137 | 2,3-dimethylphenyl | Me | —CH₂—(4-CF₃-phenyl) | |
| 138 | 2,3-dimethylphenyl | Me | —CH₂—(4-(4-chlorophenoxy)phenyl) | |
| 139 | 2,3-dimethylphenyl | Me | —CH₂—(4-(4-CF₃-phenoxy)phenyl) | |
| 140 | 2,3-dimethylphenyl | Me | —CH₂—(4-(3-chloro-5-CF₃-pyridin-2-yloxy)phenyl) | |
| 141 | 2,3-dimethylphenyl | Me | —CH₂—(4'-chloro-biphenyl-4-yl) | |
| 142 | 2,3-dimethylphenyl | Me | —CH₂—(4-(4-iPr-phenyl-diene)phenyl) | |
| 143 | 2,3-dimethoxyphenyl | Me | —CH₂—(4-Cl-phenyl) | |
| 144 | 2,3-dimethoxyphenyl | Me | —CH₂—(4-tBu-phenyl) | |
| 145 | 2,3-dimethoxyphenyl | Me | —CH₂—(4-OtBu-phenyl) | |

TABLE 1-continued

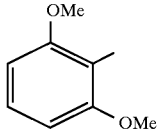

| Compound No. | $Q_1$ | $R_1$ | $Q_2$ | Physical const. Melting Point °C. Refractive Index |
|---|---|---|---|---|
| 146 | 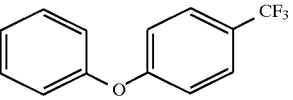 2,6-(OMe)₂-phenyl | Me | 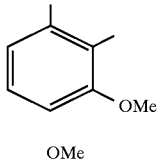 —CH₂-(4-(4-CF₃-phenoxy)phenyl) | |
| 147 | 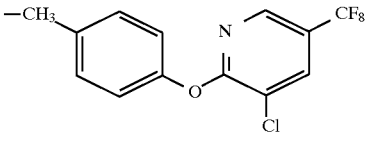 2,6-(OMe)₂-phenyl | Me | 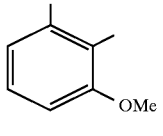 —CH₂-(4-(3-Cl-5-CF₃-pyridin-2-yloxy)phenyl) | |
| 148 | 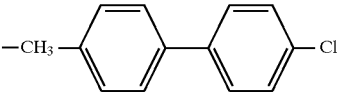 2,6-(OMe)₂-phenyl | Me | 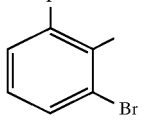 —CH₂-(4'-Cl-biphenyl) | |
| 149 | 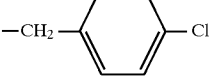 2-F-6-Br-phenyl | Me | 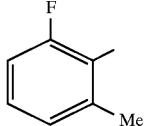 —CH₂-(4-Cl-phenyl) | |
| 150 | 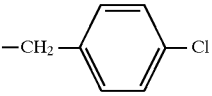 2-F-6-Me-phenyl | Me | 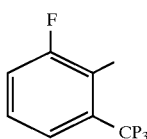 —CH₂-(4-Cl-phenyl) | |
| 151 | 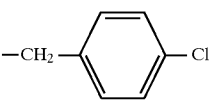 2-F-6-CF₃-phenyl | Me | 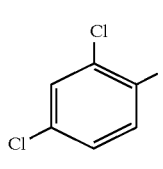 —CH₂-(4-Cl-phenyl) | |
| 152 | 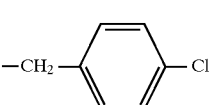 2,4-(Cl)₂-phenyl | Me | 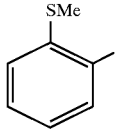 —CH₂-(4-Cl-phenyl) | |
| 153 | 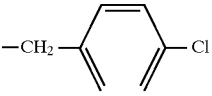 2-SMe-phenyl | Me | 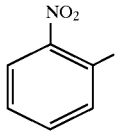 —CH₂-(4-Cl-phenyl) | |
| 154 | 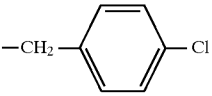 2-NO₂-phenyl | Me | —CH₂-(4-Cl-phenyl) | |

TABLE 1-continued

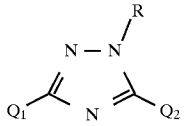

| Compound No. | $Q_1$ | $R_1$ | $Q_2$ | Physical const. Melting Point °C. Refractive Index |
|---|---|---|---|---|
| 155 | 2-NMe₂-phenyl | Me | —CH₂—(4-Cl-phenyl) | |
| 156 | 2-F,3-Cl-phenyl | —CH₂CH=CH₂ | —CH₂—(4-Cl-phenyl) | |
| 157 | 2-F,3-Cl-phenyl | —CH₂CH=CH₂ | —CH₂—(4-tBu-phenyl) | |
| 158 | 2,3-F₂-phenyl | CH₂CH=CH₂ | —CH₂—(4-Cl-phenyl) | |
| 159 | 2,3-F₂-phenyl | —CH₂CH=CH₂ | —CH₂—(4-tBu-phenyl) | |
| 160 | 2,3-Cl₂-phenyl | —CH₂CH=CH₂ | —CH₂—(4-Cl-phenyl) | |
| 161 | 2,3-Cl₂-phenyl | —CH₂CH=CH₂ | —CH₂—(4-tBu-phenyl) | |
| 162 | 2-F,3-Cl-phenyl | —CH₂—C≡CH | —CH₂—(4-Cl-phenyl) | |
| 163 | 2-F,3-Cl-phenyl | —CH₂—C≡CH | —CH₂—(4-tBu-phenyl) | |

TABLE 1-continued

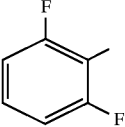

| Compound No. | $Q_1$ | $R_1$ | $Q_2$ | Physical const. Melting Point °C. Refractive Index |
|---|---|---|---|---|
| 164 | 2,6-difluorophenyl | —CH$_2$—C≡CH | —CH$_2$—(4-Cl-C$_6$H$_4$) | |
| 165 | 2,6-difluorophenyl | —CH$_2$—C≡CH | —CH$_2$—(4-$^t$Bu-C$_6$H$_4$) | |
| 166 | 2,6-dichlorophenyl | —CH$_2$—C≡CH | —CH$_2$—(4-Cl-C$_6$H$_4$) | |
| 167 | 2,6-dichlorophenyl | —CH$_2$—C≡CH | —CH$_2$—(4-$^t$Bu-C$_6$H$_4$) | |
| 168 | 2,6-difluorophenyl | —CH$_3$ | —CH$_2$—(4-OCH$_3$-C$_6$H$_4$) | $n_D^{26.5}$ 1.5679 |
| 169 | 2-F-6-Cl-phenyl | =CH$_3$ | —CH$_2$—(4-O$^t$Bu-C$_6$H$_4$) | |
| 170 | 2-F-6-Cl-phenyl | =CH$_3$ | —CH$_2$—(4-O$^n$Bu-C$_6$H$_4$) | |
| 171 | 2-F-6-Cl-phenyl | =CH$_3$ | —CH$_2$—(3-Cl-4-O$^t$Bu-C$_6$H$_3$) | |

TABLE 1-continued
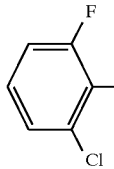
| Compound No. | Q₁ | R₁ | Q₂ | Physical const. Melting Point °C. Refractive Index |
|---|---|---|---|---|
| 172 | 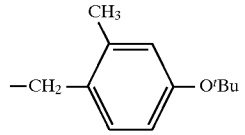 | —CH₃ | 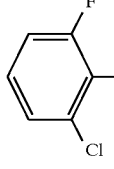 | |
| 173 | 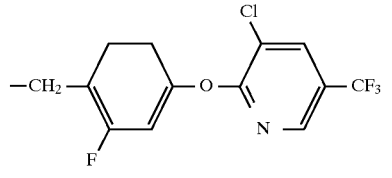 | —CH₂ | 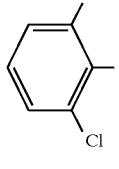 | |
| 174 | 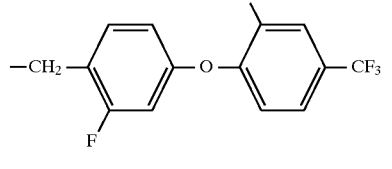 | =CH₃ | 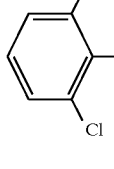 | |
| 175 | 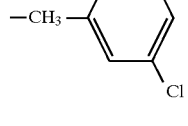 | —CH₃ | 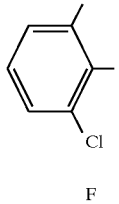 | $n_D^{24.0}$ 1.5831 |
| 176 | 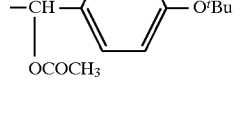 | =CH₃ | 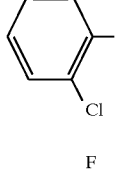 | |
| 177 | 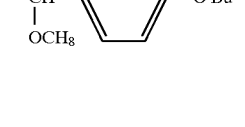 | CH₃ | 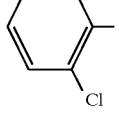 | |
| 178 | 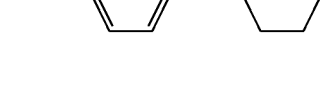 | —CH₃ | | |

TABLE 1-continued
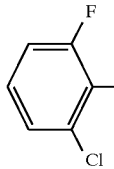
| Compound No. | Q₁ | R₁ | Q₂ | Physical const. Melting Point °C. Refractive Index |
|---|---|---|---|---|
| 179 | 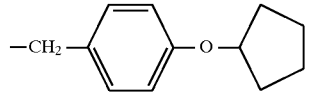 | —CH₃ | 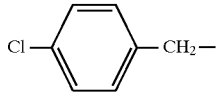 | |
| 180 | 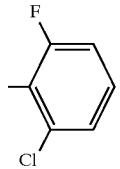 | —CH₃ | 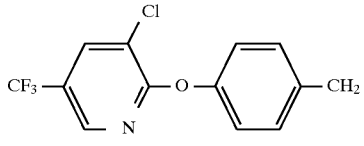 | |
| 181 | 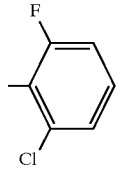 | —CH₃ | 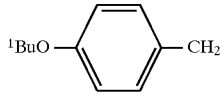 | Vis.Oil |
| 182 | 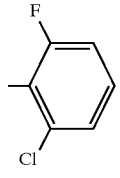 | —CH₃ | 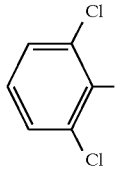 | |
| 183 | 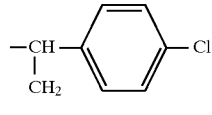 | —CH₃ | 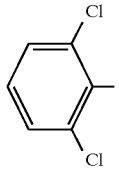 | 132–134 |
| 184 | 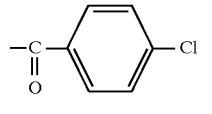 | —CH₃ | 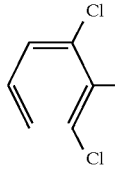 | 122–123 |
| 185 | 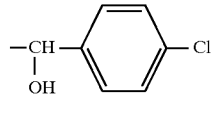 | —CH₃ | | 157–158 |

TABLE 1-continued

| Compound No. | Q₁ | R₁ | Q₂ | Physical const. Melting Point °C. Refractive Index |
|---|---|---|---|---|
| 186 | 2-F, 6-Cl-phenyl | —CH₃ | —CH₂-(4-(3-Cl-5-CCl₃-pyridin-2-yloxy)phenyl) | Vis.Oil |
| 187 | 2-F, 6-Cl-phenyl | —CH₃ | —C(O)-(4-(3-Cl-5-CCl₃-pyridin-2-yloxy)phenyl) | Amorphous |
| 188 | 2-F, 6-Cl-phenyl | —CH₃ | —CH(OH)-(4-(3-Cl-5-CCl₃-pyridin-2-yloxy)phenyl) | 188–190 |
| 189 | 2-F, 6-Cl-phenyl | —CH₃ | —C(O)-(4-(3-Cl-5-CF₃-pyridin-2-yloxy)phenyl) | 118–120 |
| 190 | 2-F, 6-Cl-phenyl | —CH₃ | —CH(OH)-(4-(3-Cl-5-CF₃-pyridin-2-yloxy)phenyl) | 165–166 |
| 191 | 2-F, 6-Cl-phenyl | —CH₃ | —CH(CH₃)-(4-(3-Cl-5-CF₃-pyridin-2-yloxy)phenyl) | $n_D^{39.6}$ 1.5293 |
| 192 | 2-F, 6-Cl-phenyl | —CH₃ | —C(CH₃)(OH)-(4-(3-Cl-5-CF₃-pyridin-2-yloxy)phenyl) | 167–168 |

TABLE 1-continued
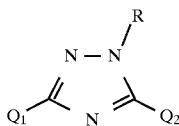
| Compound No. | $Q_1$ | $R_1$ | $Q_2$ | Physical const. Melting Point °C. Refractive Index |
|---|---|---|---|---|
| 193 | 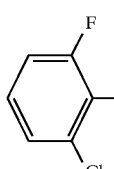 | —CH$_3$ | 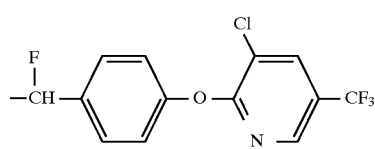 | $n_D^{23.5}$ 1.5665 |
| 194 | 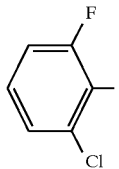 | —CH$_3$ | 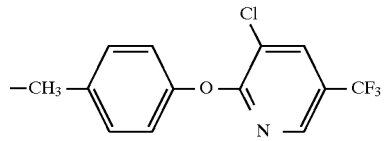 | $n_D^{23.0}$ 1.5587 |
| 195 | 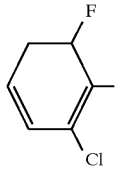 | —CH$_3$ | 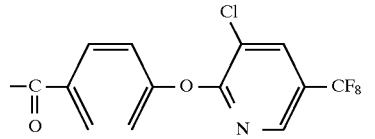 | Vis.Oil |
| 196 | 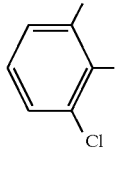 | —CH$_3$ | 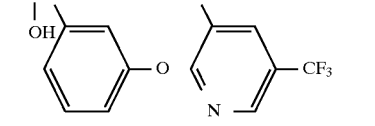 | 129–131 |
| 197 | 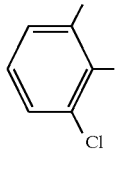 | —CH$_3$ | 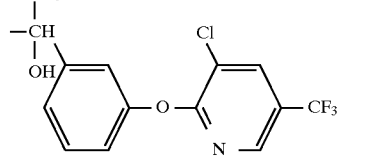 | 123–124 |
| 198 | 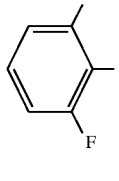 | —CH$_3$ | 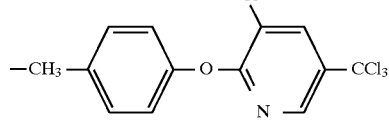 | amorphous |
| 199 | 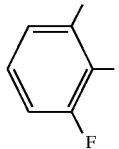 | —CH$_3$ | 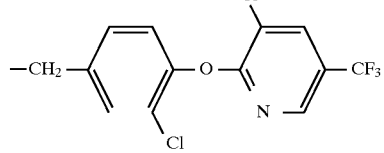 | $n_D^{22.3}$ 1.5681 |

TABLE 1-continued
| Compound No. | $Q_1$ | $R_1$ | $Q_2$ | Physical const. Melting Point °C. Refractive Index |
|---|---|---|---|---|
| 200 | 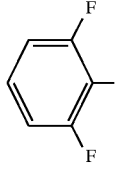 | —CH₃ | 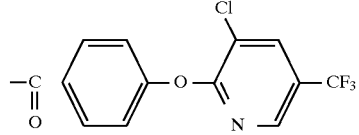 | 110–112 |
| 201 | 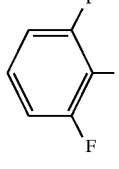 | —CH₃ | 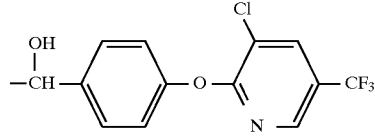 | 170–172 |
| 202 | 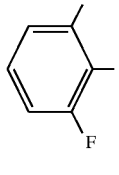 | —CH₃ | 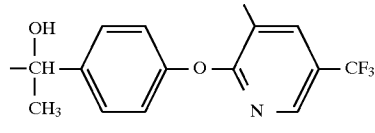 | 157–158 |
| 203 | 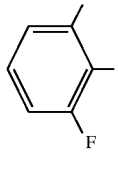 | —CH₃ | 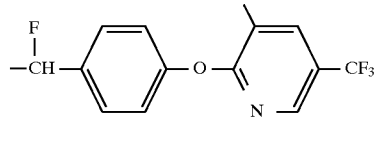 | $n_D^{29.5}$ 1.5421 |
| 204 | 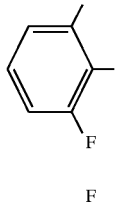 | —CH₃ | 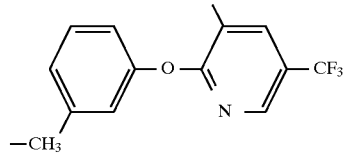 | $n_D^{24.5}$ 1.5548 |
| 205 | 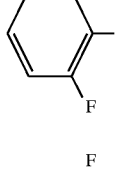 | —CH₃ | 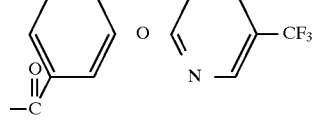 | 82–83 |
| 206 | 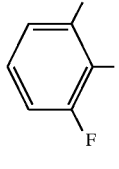 | —CH₃ | 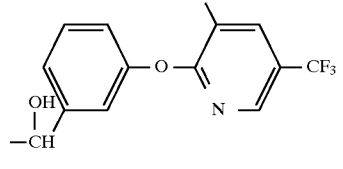 | 115–117 |

TABLE 1-continued
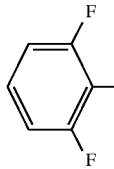
| Compound No. | Q₁ | R₁ | Q₂ | Physical const. Melting Point °C. Refractive Index |
|---|---|---|---|---|
| 207 | 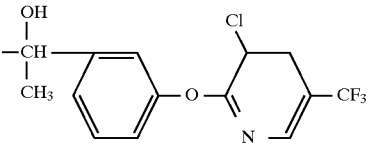 | —CH₃ | 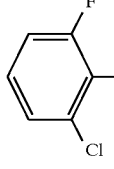 | $n_D^{25.1}$ 1.5259 |
| 208 | 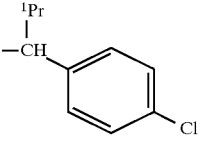 | —CH₃ | 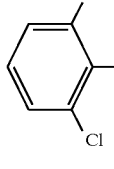 | $n_D^{25.0}$ 1.5651 |
| 209 | 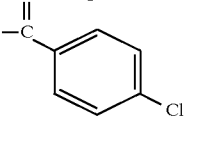 | —CH₃ | 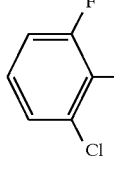 | 134–136 (isomer I) |
| 210 | 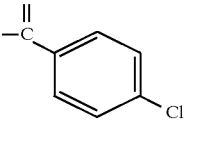 | —CH₃ | 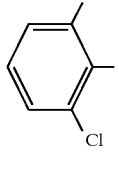 | 154–156 (isomer II) |
| 211 | 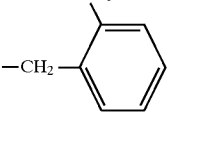 | —CH₃ | 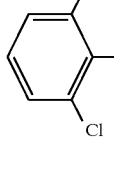 | 98–100 |
| 212 | 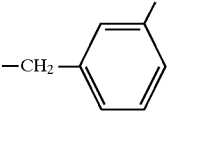 | —CH₃ | 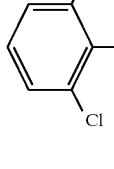 | $n_D^{28.5}$ 1.5811 |
| 213 | 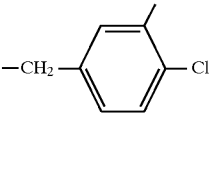 | —CH₃ | 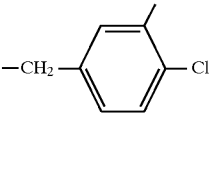 | $n_D^{23.0}$ 1.5929 |

TABLE 1-continued
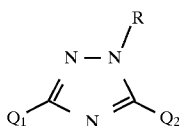
| Compound No. | Q₁ | R₁ | Q₂ | Physical const. Melting Point °C. Refractive Index |
|---|---|---|---|---|
| 214 | 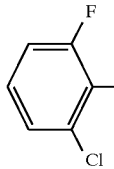 | —CH₃ | 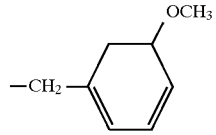 | $n_D^{24.5}$ 1.5717 |
| 215 | 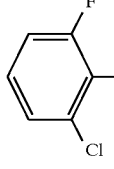 | —CH₃ | 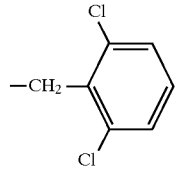 | 148–149 |
| 216 | 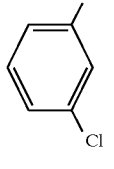 | —CH₃ | 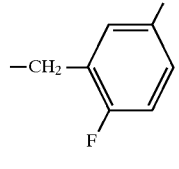 | 94–96 |
| 217 | 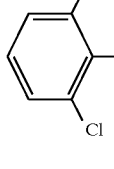 | —CH₃ | 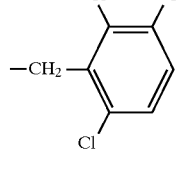 | 141–142 |
| 218 | 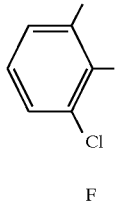 | —CH₃ | 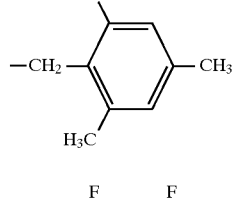 | 188–190 |
| 219 | 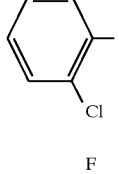 | CH₃ | 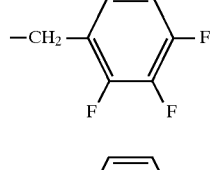 | 165–167 |
| 220 | 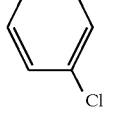 | —CH₃ | 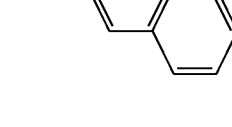 | 88–90 |

TABLE 1-continued
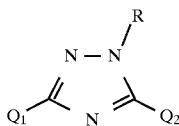
| Compound No. | Q₁ | R₁ | Q₂ | Physical const. Melting Point °C. Refractive Index |
|---|---|---|---|---|
| 221 | 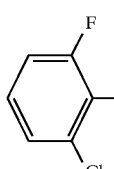 | —CH₃ | 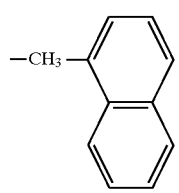 | $n_D^{20.0}$ 1.6199 |
| 222 | 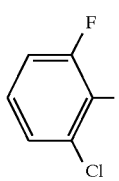 | —CH₃ | —CH₂CH₂—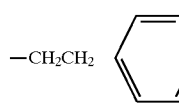 | $n_D^{22.5}$ 1.5745 |
| 223 | 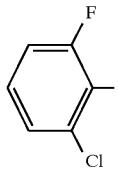 | —CH₃ | 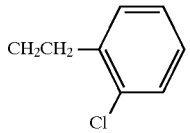 | $n_D^{28.3}$ 1.5806 |
| 224 | 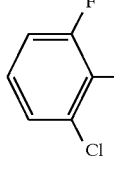 | —CH₃ | —CH₂CO—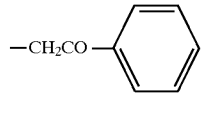 | 118–120 |
| 225 | 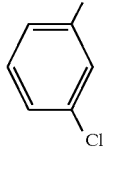 | —CH₃ | —CH₂CO—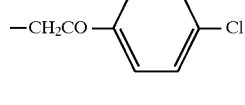 | 182–183 |
| 226 | 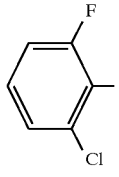 | —CH₃ | —CH=CH—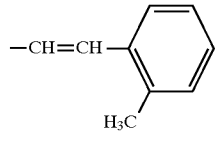 | 110–112 (trans) |
| 227 | 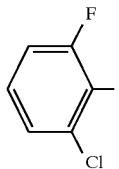 | —CH₃ | —CH—CH—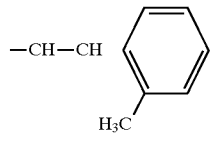 | 111–113 (cis) |

TABLE 1-continued
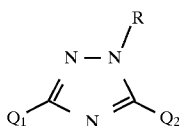
| Compound No. | Q₁ | R₁ | Q₂ | Physical const. Melting Point °C. Refractive Index |
|---|---|---|---|---|
| 228 | 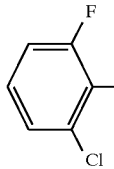 | —CH₃ | —CH—CH— 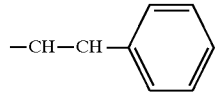 | 141–145 (trans) |
| 229 | 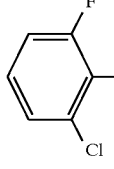 | —CH₃ | —CH=CH— 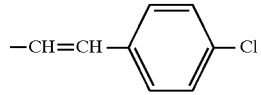—Cl | 185–186 (trans) |
| 230 | 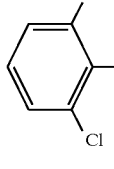 | —CH₃ | —CH=CH— 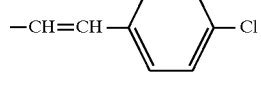—Cl | $n_D^{22.5}$ 1.6316 (cis) |
| 231 | 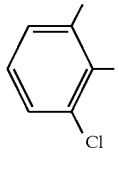 | —CH₃ | —CH=CH— 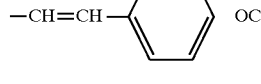OCH₈ | $n_D^{28.5}$ 1.6288 (trans) |
| 232 | 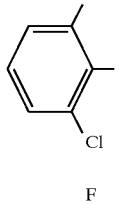 | —CH₃ | —CH₂S— 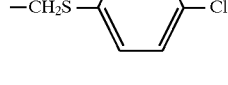—Cl | 82–83 |
| 233 | 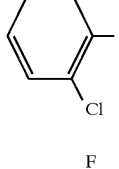 | CH₃ | —CH₂S— 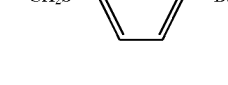—ᵗBu | $n_D^{24.5}$ 1.5579 |
| 234 | 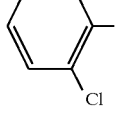 | —CH₃ | —CH₂O— 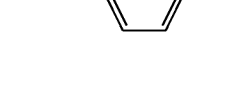—Cl | 73–76 |

TABLE 1-continued
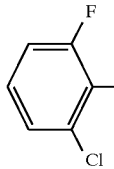
| Compound No. | Q₁ | R₁ | Q₂ | Physical const. Melting Point °C. Refractive Index |
|---|---|---|---|---|
| 235 | 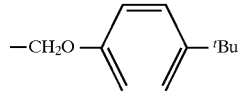 | —CH₃ | —CH₂O—⟨⟩—ᵗBu | 84–86 |
| 236 | 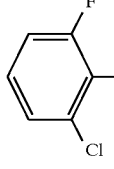 | —CH₃ | —CH₂O—⟨⟩—⟨⟩—Cl | 124–127 |
| 237 | 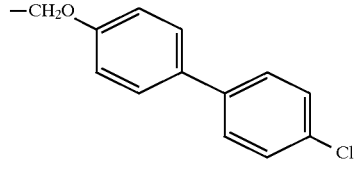 | —CH₃ | —CH₂—⟨⟩—OCOCH₃ | $n_D^{24.0}$ 1.5518 |
| 238 | 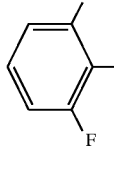 | —CH₃ | —CH₂—⟨⟩—CH₃ | 67–68 |
| 239 | 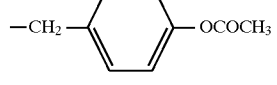 | —CH₃ | —CH₃—⟨⟩—CH₃ | $n_D^{28.5}$ 1.5699 |
| 240 | 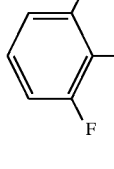 | —CH₃ | —CH₂—⟨⟩ (o-CH₃) | 104–106 |
| 241 | 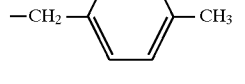 | —CH₃ | —C(O)—⟨⟩—CH₃ | 113–114 |

TABLE 1-continued
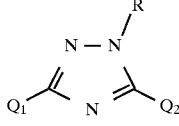
| Compound No. | Q₁ | R₁ | Q₂ | Physical const. Melting Point °C. Refractive Index |
|---|---|---|---|---|
| 242 | 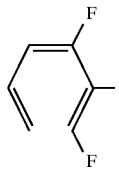 | CH₃ | 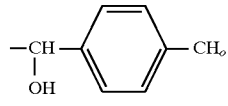 | 150–151 |
| 243 | 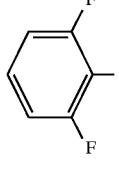 | —CH₃ | 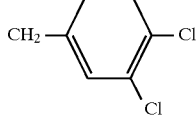 | $n_D^{26.0}$ 1.5789 |
| 244 | 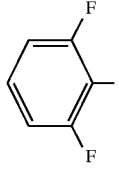 | —CH₃ | 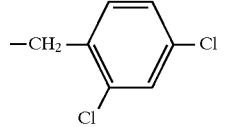 | 128–130 |
| 245 | 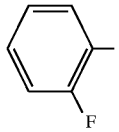 | —CH₃ | 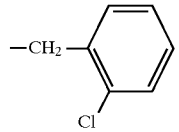 | 195–196 |
| 246 | 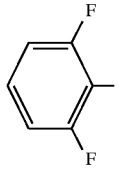 | —CH₃ | 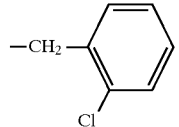 | 99–101 |
| 247 | 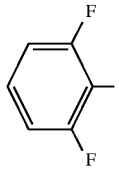 | —CH₃ | 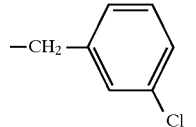 | $n_D^{24.0}$ 1.5721 |
| 248 | 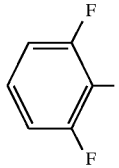 | —CH₃ | 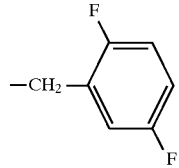 | 101–103 |
| 249 | 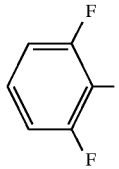 | —CH₃ | 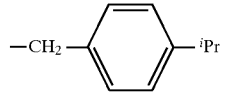 | $n_D^{28.5}$ 1.5526 |

TABLE 1-continued

| Compound No. | Q₁ | R₁ | Q₂ | Physical const. Melting Point °C. Refractive Index |
|---|---|---|---|---|
| 250 | 2,6-difluorophenyl | —CH₃ | —CH₂-(2,6,?-trichlorophenyl) | 152–153 |
| 251 | 2,6-difluorophenyl | —CH₃ | —CH₂-(2,4,6-trimethylphenyl) | 192–194 |
| 252 | 2,6-difluorophenyl | —CH₃ | —CH₂-(3-methoxyphenyl) | $n_D^{22.4}$ 1.5661 |
| 253 | 2,6-difluorophenyl | —CH₃ | —CH₂-(pentafluorophenyl) | 134–136 |
| 254 | 2,6-difluorophenyl | CH₃ | —CH₃-(naphth-2-yl) | 123–125 |
| 255 | 2,6-difluorophenyl | —CH₃ | —CH₃-(naphth-1-yl) | $n_D^{22.0}$ 1.0132 |
| 256 | 2,6-difluorophenyl | —CH₃ | —CH₂CH₂-phenyl | $n_D^{22.5}$ 1.5624 |

TABLE 1-continued
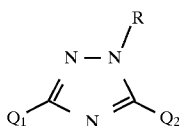
| Compound No. | $Q_1$ | $R_1$ | $Q_2$ | Physical const. Melting Point °C. Refractive Index |
|---|---|---|---|---|
| 257 | 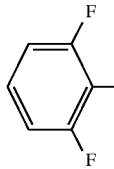 | —CH$_3$ | 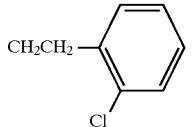 | $n_D^{22.5}$ 1.5693 |
| 258 | 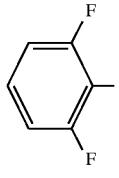 | —CH$_3$ | 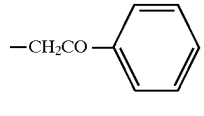 | 121–123 |
| 259 | 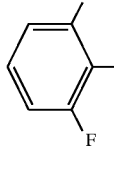 | —CH$_3$ | 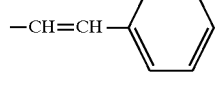 | 107–109 (trans) |
| 260 | 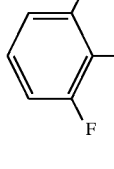 | —CH$_3$ | 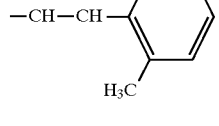 | 108–110 (trans) |
| 261 | 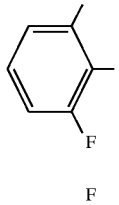 | —CH$_3$ | 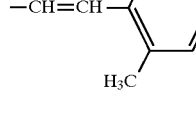 | 80–82 (cis) |
| 262 | 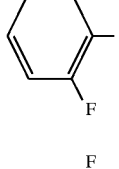 | —CH$_3$ | 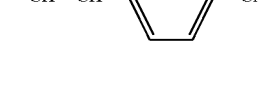 | 115–116 (trans) |
| 263 | 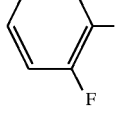 | —CH$_3$ | 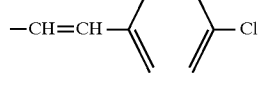 | 56–57 (cis) |

TABLE 1-continued
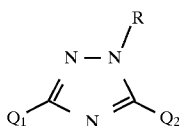
| Compound No. | $Q_1$ | $R_1$ | $Q_2$ | Physical const. Melting Point °C. Refractive Index |
|---|---|---|---|---|
| 264 | 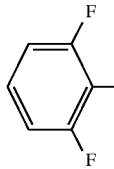 | —CH₃ | 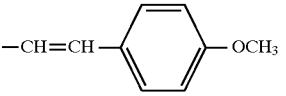 | $n_D^{28.8}$ 1.6208 (trans) |
| 265 | 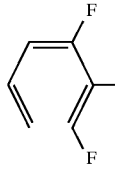 | —CH₃ | 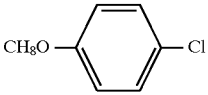 | 99–101 |
| 266 | 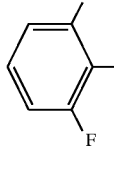 | —CH₃ | 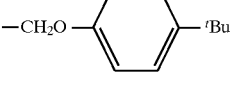 | 111–113 |
| 267 | 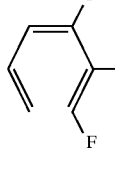 | —CH₃ | 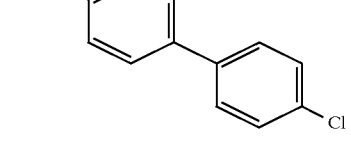 | 134–136 |
| 268 | 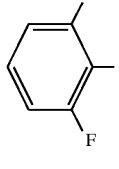 | —CH₃ | 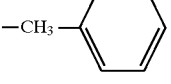 | 97–99 |
| 269 | 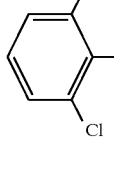 | —C₃H₅ | 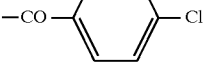 | 86–88 |
| 270 | 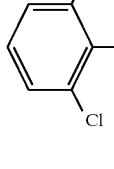 | ⁿPr | 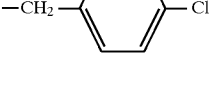 | $n_D^{27.6}$ 1.5672 |

TABLE 1-continued
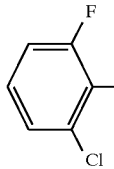
| Compound No. | $Q_1$ | $R_1$ | $Q_2$ | Physical const. Melting Point °C. Refractive Index |
|---|---|---|---|---|
| 271 | 2-F, 6-Cl-phenyl | nPr | —CO—C6H4—Cl (4-) | 61–62 |
| 272 | 2-F, 6-Cl-phenyl | nBu | —CO—C6H4—Cl (4-) | 62–63 |
| 273 | 2-F, 6-Cl-phenyl | nHex | —CH2—C6H4—Cl (4-) | $n_D^{24.4}$ 1.5588 |
| 274 | 2-F, 6-Cl-phenyl | nHex | —CO—C6H4—Cl (4-) | 69–71 |
| 275 | 2-F, 6-Cl-phenyl | nOct | —CH2—C6H4—Cl (4-) | $n_D^{28.2}$ 1.5476 |
| 276 | 2-F, 6-Cl-phenyl | nOct | —CO—C6H4—Cl (4-) | $n_D^{22.8}$ 1.6700 |
| 277 | 2-F, 6-Cl-phenyl | Bt | —CH8—C6H4—OMe | $n_D^{26.0}$ 1.5667 |

TABLE 1-continued
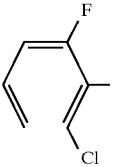
| Compound No. | Q₁ | R₁ | Q₂ | Physical const. Melting Point °C. Refractive Index |
|---|---|---|---|---|
| 278 |  | $^i$Pr | 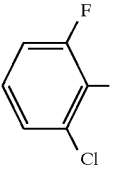 —CH₂—⟨⟩—OMe | 81–84 |
| 279 | 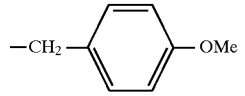 | $^n$Pr | —CH₂—⟨⟩—OMe | $n_D^{28.5}$ 1.5617 |
| 280 | 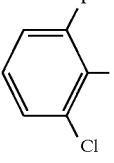 | $^n$Bu | —CH₂—⟨⟩—OMe | 86–88 |
| 281 |  | $^n$Hex | —CH₂—⟨⟩—OMe | $n_D^{24.6}$ 1.5489 |
| 282 | 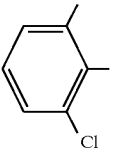 | $^n$Oct | —CH₂—⟨⟩—OMe | $n_D^{22.5}$ 1.5458 |
| 283 | 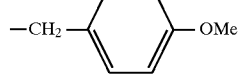 | CH₃ | 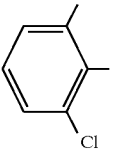 | Amorphous |
| 284 | 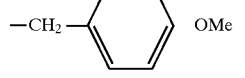 | CH₃ | 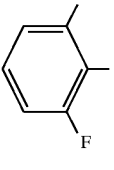 | Amorphous |

TABLE 1-continued

| Compound No. | Q₁ | R₁ | Q₂ | Physical const. Melting Point °C. Refractive Index |
|---|---|---|---|---|
| 285 | 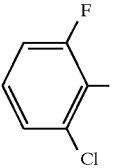 2-F, 6-Cl phenyl | CH₃ | 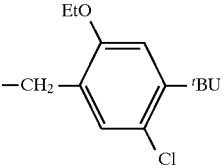 —CH₂— (EtO, tBu, Cl substituted phenyl) | $n_D^{26.5}$ 1.6463 |
| 286 | 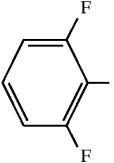 2,6-diF phenyl | CH₃ | 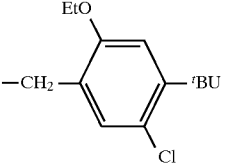 —CH₂— (EtO, tBu, Cl substituted phenyl) | 144–147 |
| 287 | 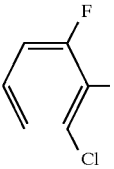 | CH₃ | 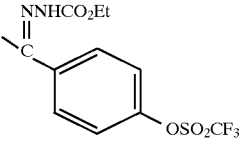 C(=NNHCO₂Et)-phenyl-OSO₂CF₃ | 130–133 (Isomer I) |
| 288 | 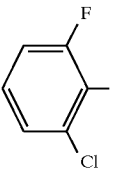 2-F, 6-Cl phenyl | CH₃ | 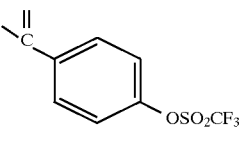 C(=NNHCO₂Et)-phenyl-OSO₂CF₃ | 154–156 (Isomer II) |
| 289 | 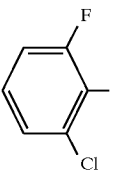 2-F, 6-Cl phenyl | CH₃ | 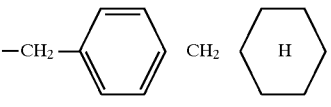 —CH₂—phenyl—CH₂—cyclohexyl (H) | 117–119 |
| 290 | 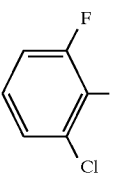 2-F, 6-Cl phenyl | Et | 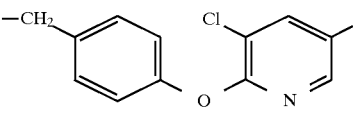 —CH₂—phenyl—O—(3-Cl, 5-CF₃ pyridinyl) | 108–109 |
| 291 | 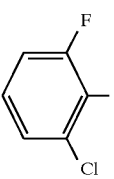 2-F, 6-Cl phenyl | iPr | 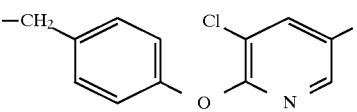 —CH₂—phenyl—O—(3-Cl, 5-CF₃ pyridinyl) | 109–111 |

TABLE 1-continued
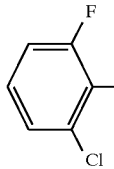
| Compound No. | Q₁ | R₁ | Q₂ | Physical const. Melting Point °C. Refractive Index |
|---|---|---|---|---|
| 292 | 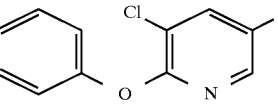 | ⁿPr | 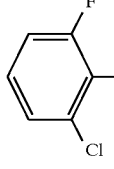 | $n_D^{26.8}$ 1.5500 |
| 293 | 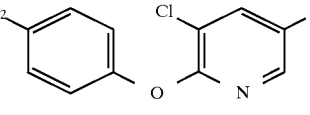 | ⁿBu | 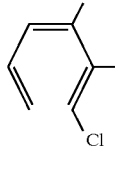 | $n_D^{27.0}$ 1.5480 |
| 294 | 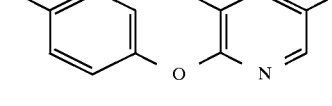 | ⁿHex | 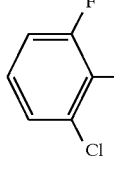 | $n_D^{25.8}$ 1.5423 |
| 295 | 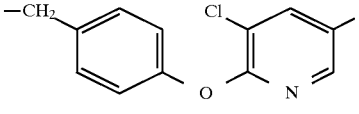 | ⁿOct | 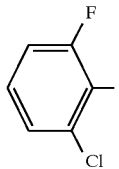 | $n_D^{22.7}$ 1.5391 |
| 296 | 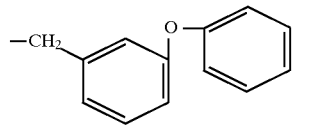 | CH₃ | 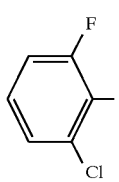 | $n_D^{22.5}$ 1.5819 |
| 297 | 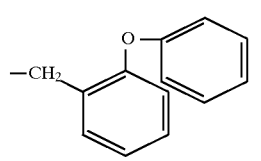 | CH₃ | 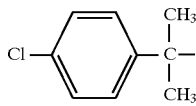 | $n_D^{28.5}$ 1.5044 |
| 298 | 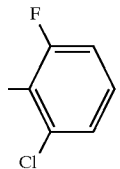 | CH₃ |  | 97–100 |

TABLE 1-continued

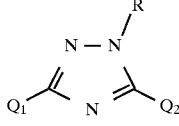

| Compound No. | Q₁ | R₁ | Q₂ | Physical const. Melting Point °C. Refractive Index |
|---|---|---|---|---|
| 299 | 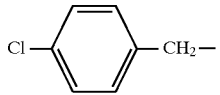 4-Cl-C₆H₄-CH₂— | $CH_3$ | 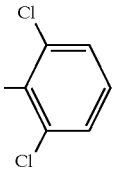 2,6-diCl-C₆H₃— | 77–80 |
| 300 | 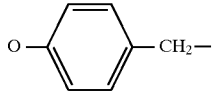 4-O-C₆H₄-CH₂— | $CH_3$ | 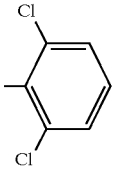 2,6-diCl-C₆H₃— | 89–90 |
| 301 | 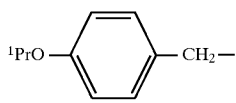 4-iPrO-C₆H₄-CH₂— | $CH_3$ | 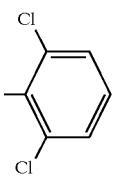 2,6-diCl-C₆H₃— | 86–87 |
| 302 | 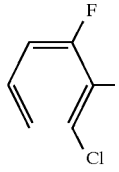 | $CH_3$ | 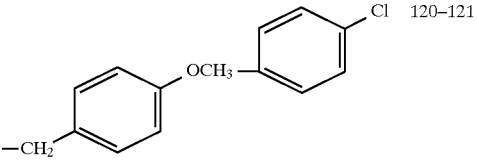 —CH₂-C₆H₄-OCH₃-C₆H₄-Cl | 120–121 |
| 303 | 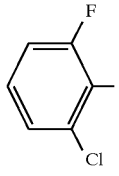 2-F-6-Cl-C₆H₃— | $CH_3$ | 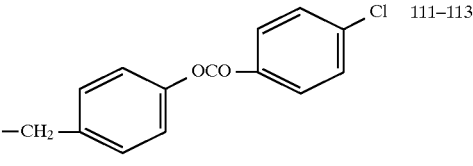 —CH₂-C₆H₄-OCO-C₆H₄-Cl | 111–113 |

¹H-NMR Spectrum Data (dTMS, CDCl₂, ppm)

No. 79:
3.78(s, 3H), 4.12(s, 2H), 6.62(d, 2H), 6.88–7.42(m,5H), 8.12(br, 1H)

No. 80:
2.28(s, 3H), 3.80(s, 3H), 4.24(s, 2H), 6.95 –7.44(m, 7H)

No. 81:
3.81(s, 3H), 4.12(s, 2H), 6.63(d, 2H), 6.88–7.42(m, 5H), 7.85(br, 1H)

No. 82:
2.30(s, 3H), 3.80(s,3H), 4.25(s, 2H), 6.93–7.09(m, 4H), 7.22 –7.42(m, 3H)

No. 181:
3.72(s, 3H), 4.18(s, 2H), 7.08–7.53(m, 7H), 7.98(d, 1H), 8.27(d, 1H)

No. 186:
3.82(s, 3H), 4.28(s, 2H), 7.03–7.40(m, 7H), 8.26(d, 1H), 8.54(d, 1H)

No. 187:
4.33(s, 3H), 7.03–7.64 (m, 5H), 8.00–8.43(m, 4H)

No. 194:
3.82(s, 3H), 4.29(s, 2H), 7.01–7.47(m, 7H), 7.97(d, 1H), 8.23(d, 1H)

No. 195:
4.34(s, 3H), 7.07–7.43(m, 5H), 8.30(d, 1H), 8.52–8.62(m, 3H)

No. 108:
3.82(s, 3H), 4.30(s, 2H), 7.00(t, 2H), 7.10–7.45(m, 5H), 8.26(d, 1H), 8.56(d, 1H)

No. 283:
1.28(s, 9H) 4.01(s, 3H), 4.12(s, 2H), 6.87–6.93(m, 1H), 7.02–7.37(m, 5H), 9.41 (brs, 1H)

No. 284:
1.28(s, 9H), 4.01(s, 3H), 4.12(s, 2H), 6.87–7.42(m, 6H), 9.72(brs, 1H)

The compounds of the present invention can be used for the control of pests against agricultural production, hygienic peat insects, pest in sects in storing grains, pest insects of clothing, house pest insects, etc. The representative examples for such pests are exemplified herinbelow.

For examples or Lepidopterous pest insects, cotton leafworm, cabbage armyworm, black cutworm, common cabbageworm, cabbage looper, diamond-back, smaller tea tortrix, tea leaf roller, peach fruit moth, oriental fruit moth, citrus leaf miner, tea leaf roller, apple leaf miner, gypsy moth, tea tussock moth, rice stem borer, grass leaf roller, European corn borer, fall webworm, almond moth, *Heliothis sp., Helicoverpa sp., Agrotis sp.*, casemaking clothes moth, codling moth, and cotton ballworm are exemplified. For examples of Hemipterous pest insects, green peach aphid, cotton aphid, turilip aphid, grain aphid, bean bug, common green stink bug, arrowhead scale, mulberry mealy scale, greenhouse whitefly, tobacco whitefly, pear psylla, Japanese pear lace bug, brown planthopper, small brown planthopper, white-backed planthopper, and green rice leafhopper are exemplified. For examples of Coleopterous pest insects, striped flea beetle, cucurbit leaf beetle, Colorado potato beetle, rice water weevil, rice weevil, azuki bean weevil, Japanese beetle, soybean beetle, *Diabrotica sp.*, cigarette beetle, powder post beetle, pine sawyer, white-spotted longicorn beetle, *Agriotis sp.*, 28-spotted ladybeetle. rust-red flour beetle, and cotton ball weevil are exemplified. For examples of Dipterous harmful insects, housefly, *Calliphora lata, Boettcherisca peregrina*, cucurbit fruit fly, citrus fruit fly, seed maggot, rice leaf miner, yellow drosophila, *Stomoxys calcitrans, Culox tritaeniarhynchus, Aedes aegypti.* and *Anopheles hyrcanus*, are exemplified. For example of Thysanopt erous pest insects. *Thrips palmi*, and tea thrips are exemplified. For examples of Hymcnopterus harmful insects, *Monomorium pharaonis*. Yellow harnet and cabbage sawfly are exemplified. For examples of Orthopterous harmful insects. German cockroach, American cockroach, Japanese cockroach, and grasshopper are exemplified. Isopterous harmful insects, such as Formosan subterranean termite and *Reticulitermes speratus* Kolbe, Aphanipterous harmful insects such as human flea, Anoplurous harmful insects such as human louse, mites, such as two-spotted spider mite, carmine spider mite, Kanzawa spider mite, citrus red mite, European red mite, citrus rust mite, apple rust mite, *Tarsonemus sp., Brevipalpus sp., Eotetranychus sp.*, Robin bulb mite, common grain mite, *Desmatophagoides farinae, Boophilus microplus* and *Haemaphysallis bispinosa*, plant-parasitic nematodes, such as southern root-knot nematode, root lesion nematode, soybean cyst namatode, rice white-tip nematode and pine wood nenatode are exemplified.

In recent years, numerous species of harmful insects such as diamondback moth, planthopper, and leafhopper have come to build tolerance to organophosphate reagents, carbamate reagents, and acaricides. The inability of these reagents to manifest necessary effects has been posing a serious problem. A need has arisen for chemical reagents which are capable of effectively destroying harmful insects and mites of the species which have built tolerance. The compounds according to this invention are chemical reagents which manifest satisfactory insecticidal and acaricidal effects not only to insects and mites of the aesthetic species but also to the insects of the species tolerating carbamate reagents and pyrothroid reagents and the mites of the species tolerating acaricides.

Further, the compounds according to this invention produce only sparlngly low toxicity, do only insignificant harm to fish and hybrid animals, and enjoy pronnounced safety.

The compounds according to this invention ran also be used as antifueling agents for preventing aquatic organisms from attaching to ship bottoms and fish nets.

[Insocticidal and acaricidal agents]

The compounds according to this invention which are produced as described above can be used for actual application in their pure form, namely without addition of other components. For application in agriculture, they may be prepared in various forms allowed for standard agricultural chemicals such as, for example, wettable powders, granules, dusts, emulsifiable concentrates, solutions, suspensions, and flowable powders.

As additives and carriers for solid preparations, plant powders such as soybean grains and flour, finely powdered mineral materials such as diatomaceous earth, lime, gypsum, talc, bentonite, pyrophyllite, and clay, and organic and inorganic compounds such as sodium benzoate, urea, and Glauber's salt. For liquid preparations, oil fractions such as kerosine, xylene, and solvent naphtha, cyclohexane, cyclohexa-none, dimethyl formamide, dimethyl sulfoxide, alcohols, acetone, trichloroethylene, methylisobutyl ketone, mineral oils. vegetable oil, and water are used as solvents. These preparations allow addition thereto of a surfactant when necessary for the purpose of assuming a homogeneous and stable form. Properly, these preparations contain the compound as an active component at a concentration in the range of 5 to 70%. The wettable powder, emulsion, and flowable agent are diluted with water to prescribed concentrations and are used in the form of a suspension or emulsion and the dust and granules are sprayed in their unmodified forms.

As typical examples of the fungicide, insecticide, acaricide, and plant growth regulator which can be effectively used as mixed with the compounds of this invention, the following compounds may be cited.

[Fungicides]

Captan, fulpet, thiuram, ziram, zineb, manneb, mankozeb, propineb, polycarbamate, chloroethanol, quintozene, captafol, iprodione, procymidone, vinclozoline, fluoroimide, simoxanyl, mepronyl, flutranyl, pencycron, oxycarboxin, fosethyl-aluminium, propamocarb, triadimefon, triadimenol, propiconazol, diclobutrazol, bitertanol, hexaconazol, microbutanil, flusilazole, etaconazole, fluotrimazole, flutriafol, penconazole, diniconazole, cyproconazole, fenarimol, triflumizole, procloraz, imazalil, peflazoate, tridemorph, fenpropimorph, trifolin, buthiobate, pyrifenox, anilazine, polyoxin, metalaxyl, oxadixyl, furalaxyl, isoprothiolane, probenazole, pyrrolnitrin, blastocidin-S, kasugamycin, validamycin, dihydrostreptomycin sulphate, benomyl, carbedazim, thiophanate methyl, hymexazol, basic cupric chloride, basic cupric sulphate, fentin acetate, fentin hydroxide, diethofencarb, methasulfocarb, chinomethionat, binapacryl, lecithin, sodium bicarbonate, dithianone, dinocap, fenaminosulf, dichlomezine, guazatin, dodine, TBP, edifenphos, mepanipyrium, ferinmzone, trichlamide, methasulfocarb, fluazinam, oxolinic acid, dimethomorph, pyroquilon, techlophthalam, fthalide, fenazino oxide, thiabendazole, vinclozfolin, cymoxanil, myclobutanil, guazatine, propamocarb hydrochloride, oxolinic acid.

[Organophosphorus and Carbamate Insecticides]

Fenthion, fenitrothion, diazinon, chlorpyriphos, ESP, vamidothion, fenthoate, dimethoate, formothion, malathion, trichlorfon, thiometon, phosmet, dichlorvos, acephate, EPBP, methyl parathion, oxydimedon methyl, ethion, salithion, cyanophos, isoxathion, pyridafenthion, phosalon, methidathion, sulprophos, chlorfevinphos, tetrachlorvinphos, dimethylvinphos, propaphos, isofenphos, ethylthiometon, prophenophos, pyracrophos, monocrotophos, azinphos methyl, aldicarb, methomyl, thiodicarb, carbofuran, carbosulfan, benfuracarb, flathiocarb, propoxur, BPMC, MTMC, MIPC, carbaryl, pirimicarb, ethiophencarb, phenoxycarb, cartap, thiocyclam, bensultap, etc.

[Pyrethroid insecticides]

Permethrin, cypermethrin, deltamethrin, fenvalerate, fenpropathrin, pyrethrin, allethrin, tetramethrin, resmethrin, dimethrin, propathrin, fenothrin, prothrin, phluvalinate, cyfluthrin, cyhalothrin, flucythrirnate, ethofenprox, cycloprothrin, tralomethrin, silafluophen, brofendrox, acrinathrin, etc.

[Benzoylphenylureas and other insecticides]

Diflubanzuron, chlorfluazuron, hexaflumuron, triflumuron, teflubenzuron, flufenoxuron, flucycloxuron, buprofezin, pyriproxyfen, methoprene, benzoepin, diafenthiuron, imidacloprid, fipronil, nicotin sulfate, rotenone, meta-aldehyde, machine oll, *Bacillus thuringiensis*, microbial insecticides such as insect-pathogenic viruses, etc.

[Nematocides]

Fenamiphos, phosthiazate, etc.

[Acaricides]

Chlorbenezilate, phenisobromolate, dicofol, amitraz, BPPS, benzomate, hexythiazox, fenbutatin oxide, pulynactin, quinomethionate, CPCBS, tetradifon, avermectin, milbemectin, clofentezin, cyhexatin, pyridaben, fenpyroxymate, tebufenpyrad, pyrimidifen, fenothiocarb, dienochlor, etc.

[Plant growth regulators]

Gibberellins (gibberelli $A_8$, gibberelli $A_4$, gibberelli $A_7$ etc.), IAA, NAA

[Working Examples]
[Insecticides and acaricides]

Now, several working examples of the composition of this invention will be cited below. It should be noted, however, that the additives and the proportions of their addition in the compositions need not be limited to those indicated in the working examples but may be varied in wide ranges. The "parts" mentioned in the working examples are "parts by weight."

Example 7 (Wettable powder)

Compound of this invention 40 parts

Diatomaceous earth 53 parts

Higher alcohol sulfuric ester 4 parts

Alkylnaphthalene sulfonate 3 parts

A wettable powder containing an active component at a concentration of 40% is obtained by homogenously mixing these components and finely pulverizing the resultant mixture.

Example 8 (Emulsifiable concentrate)

Compound of this invention 30 parts

Xylene 33 parts

Dimethyl formamide 30 parts

Polyoxyethylene alkylallyl other 7 parts

An emulsion containing an active component at a concentration of 30% is obtained by mixing these components until thorough solution.

Example 9 (Dust)

Compound of this invention 10 parts

Talc 89 parts

Polyoxyethylene alkylallyl ether 1 Part

A dust containing an active component at a concentration of 10% is obtained by homogeneously mixing these components.

Example 10 (Granules)

Compound of this invention 5 parts

Clay 73 parts

Bentonite 20 parts

Sodium dioctylsulfosucoinate 1 part

Sodium phosphate 1 part

Granules containing an active component at a concentration of 5% were obtained by thorouthly pulveriazing and mixingt these components, thoroughly kneading the resultant mixture with water, and thereafter pelletizingt the blend and drying the produced pellets.

Example 11 (Suspension)

Compound of this invention 10 parts

Sodium ligninsulfonate 4 parts

Sodium dodecylbenzenesulfonate 1 part

Xanthan gum 0.2 part

Water 84.8 parts

A suspensinon containing an active component at a concentration of 10% is obtained by wet pulverizing the components until a particle size of not more than 1 micron is obtained.

EFFECT OF THE INVENTION

Test Example 1 (Effect against cotton aphid)

The cucumbers sown in pots 3 suns (about 3.6 inches) in diameter and grown for 10 days after germination were inoculated with imagoes of cotton aphid. One day thereafter, the imagoes were removed from the cucumbers and the cucumbers infested by the nymphs yielded thence by the imagoes were sprayed with a chemical solution prepared by diluting the emulsifiable concentrate of the formulation of Example 8 with water to a compound concentration of 125 ppm. The cucumbers were left standing in a constant temperature chamber kept at a temperature of 25° C. and a humidity of 05%. Six days thereafter, the cucumbers were examined to determine the ratio of extirpation. The results are shown in Table 2.

TABLE 2

| Compound No. | mortality (%) |
|---|---|
| 2 | 100 |
| 3 | 100 |
| 4 | 100 |
| 5 | 100 |
| 7 | 100 |
| 9 | 100 |
| 14 | 100 |
| 15 | 100 |
| 18 | 100 |
| 19 | 100 |
| 20 | 100 |
| 21 | 100 |
| 27 | 100 |
| 31 | 100 |
| 33 | 100 |
| 92 | 100 |
| 95 | 100 |

TABLE 2-continued

| Compound No. | mortality (%) |
|---|---|
| 104 | 100 |
| 105 | 100 |
| 108 | 100 |
| 110 | 100 |
| 175 | 100 |
| 183 | 100 |
| 184 | 100 |
| 185 | 100 |
| 208 | 100 |
| 211 | 100 |
| 212 | 100 |
| 213 | 100 |
| 216 | 100 |
| 220 | 100 |
| 221 | 100 |
| 223 | 100 |
| 224 | 80 |
| 226 | 100 |
| 228 | 100 |
| 234 | 100 |
| 241 | 100 |
| 242 | 83 |
| 246 | 83 |
| 257 | 83 |
| 259 | 84 |
| Reference Compound A | 0 |
| Reference Compound B | 100 |

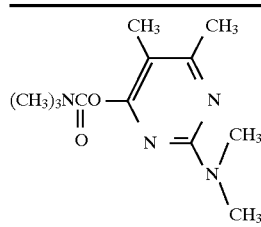

Reference Compound A (Pirimicarb)

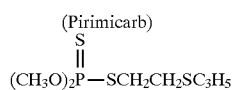

Reference Compound B (Thiometon)

Test Example 2 (Effect against two-spotted spider mite)

The kidney beans sown in pots 2 suns (equivalent to about 2.3 inches) in diameter were grown. To the primary leaves of the plants grown for seven to ten days after germination, 17 adult females imagoes of two-spotted spider mites, which is resistant strain to organo phosphate reagents were inoculated and were sprayed with a chemical solution prepared by diluting the wettable powder of the formulation of Example 7 with water to a compound concentration of 125 ppm. The kidney beans were left growing in a constant temperature room kept at a temperature of 25° C. and a humidity of 65%. Three days after the spray, the adults were removed from the plants. On the 11th day in the room, the plants were examined to determine whether or not the eggs oviposited by the adults during the three days mentioned had developed to the stage of adult and rate tho ratio of extirpation. The results are shown in Table 3. The ratio of extirpation was determined in accordance with the following formula.

Ratio of extirpation (%)=[(Number of adults in the non-treated plot)−(Number of adults in the treated plot)]÷Number of adults in the non-treated plot)×100

TABLE 3

| Compound No. | mortality (%) |
|---|---|
| 1 | 99 |
| 2 | 100 |
| 3 | 97 |
| 4 | 98 |
| 5 | 100 |
| 6 | 98 |
| 7 | 100 |
| 8 | 100 |
| 9 | 100 |
| 15 | 97 |
| 17 | 100 |
| 18 | 100 |
| 19 | 100 |
| 20 | 100 |
| 21 | 100 |
| 27 | 100 |
| 31 | 93 |
| 33 | 100 |
| 53 | 100 |
| 60 | 100 |
| 70 | 98 |
| 75 | 100 |
| 76 | 100 |
| 91 | 100 |
| 95 | 99 |
| 96 | 99 |
| 97 | 100 |
| 101 | 100 |
| 104 | 100 |
| 105 | 100 |
| 107 | 100 |
| 108 | 100 |
| 110 | 100 |
| 114 | 100 |
| 168 | 93 |
| 175 | 93 |
| 183 | 100 |
| 184 | 100 |
| 185 | 100 |
| 186 | 98 |
| 189 | 98 |
| 190 | 99 |
| 191 | 100 |
| 192 | 100 |
| 193 | 100 |
| 194 | 99 |
| 195 | 100 |
| 196 | 100 |
| 197 | 100 |
| 198 | 100 |
| 199 | 99 |
| 200 | 99 |
| 201 | 100 |
| 202 | 100 |
| 203 | 99 |
| 204 | 99 |
| 205 | 100 |
| 206 | 100 |
| 207 | 99 |
| 209 | 100 |
| 210 | 99 |
| 211 | 95 |
| 213 | 100 |
| 216 | 99 |
| 217 | 100 |
| 220 | 99 |
| 229 | 100 |
| 230 | 100 |
| 233 | 100 |
| 234 | 100 |
| 235 | 100 |
| 236 | 100 |
| 243 | 100 |
| 247 | 97 |
| 249 | 99 |

TABLE 3-continued

| Compound No. | mortality (%) |
| --- | --- |
| 254 | 99 |
| 255 | 98 |
| 262 | 96 |
| 263 | 100 |
| 265 | 94 |
| 266 | 100 |
| 267 | 100 |
| 268 | 100 |
| 269 | 99 |
| 270 | 100 |
| 271 | 97 |
| 277 | 98 |
| 287 | 99 |
| 288 | 99 |
| 289 | 100 |
| 290 | 99 |
| 291 | 100 |
| 292 | 100 |
| 293 | 100 |
| 294 | 100 |
| 296 | 98 |
| Reference compound C | 55 |

Reference cmpound C

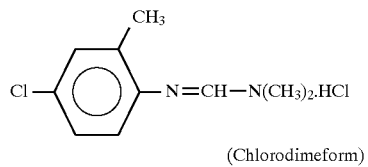

(Chlorodimeform)

TABLE 4

| Compound No. | mortality (%) |
| --- | --- |
| 3 | 100 |
| 5 | 100 |
| 6 | 100 |
| 7 | 100 |
| 18 | 90 |
| 31 | 80 |
| 70 | 100 |
| 75 | 100 |
| 76 | 100 |
| 101 | 80 |
| 183 | 90 |
| 184 | 100 |
| 185 | 100 |
| 189 | 100 |
| 190 | 100 |
| 191 | 100 |
| 192 | 100 |
| 193 | 90 |
| 194 | 80 |
| 200 | 100 |
| 201 | 100 |
| 202 | 90 |
| 209 | 100 |
| 210 | 90 |
| 217 | 80 |
| 228 | 80 |
| 236 | 93 |
| 271 | 100 |
| 291 | 100 |
| 292 | 100 |
| 294 | 90 |
| Reference Compound C | 40 |

TABLE 4-continued

| Compound No. | mortality (%) |
| --- | --- |

Reference Compound C

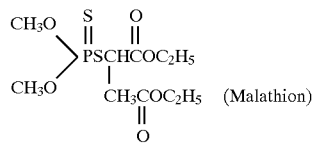

(Chlorodimeform)

TABLE 5

| Compound No. | mortality (%) |
| --- | --- |
| 1 | 100 |
| 2 | 100 |
| 3 | 87 |
| 4 | 100 |
| 5 | 100 |
| 14 | 100 |
| 15 | 100 |
| 17 | 100 |
| 18 | 100 |
| 19 | 100 |
| 31 | 100 |
| 91 | 100 |
| 104 | 100 |
| 105 | 100 |
| 107 | 100 |
| 175 | 90 |
| 211 | 100 |
| 212 | 90 |
| 216 | 100 |
| 238 | 100 |
| 268 | 100 |
| Reference Compound D | 0 |

Refenrence Compound D

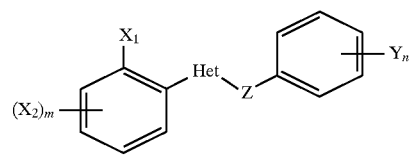

Industrial Applicability:

As described above, the compounds according to this invention manifest pronounced insecticidal and acaricidal activities and are useful as insecticides and acaricides in agriculture and horticulture.

What is claimed is:

1. A triazole compound represented by the formula (1) or a salt of formula (1):

wherein Het =

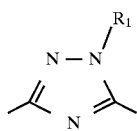

(a) or

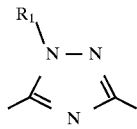

(b)

X₁ represents a halogen atom, a $C_{1-C_6}$ alkyl group, a $C_1$–$C_6$ alkoxy group, a $C_1$–$C_6$ haloalkyl group, a $C_1$–$C_6$ alkylthio group, a nitro group, or a $C_1$–$C_6$ alkylamino group;

X₂ represents a halogen atom, a $C_1$–$C_6$ alkyl group, or a $C_1$–$C_6$ alkoxy group;

Y represents an optionally substituted pyridyloxy group optionally substituted by a halogen atom, a $C_1$–$C_6$ alkyl group or a $C_1$–$C_6$ haloalkyl group;

R₁ represents a $C_1$–$C_6$ alkyl group, a $C_2$–$C_6$ alkenyl group, a $C_2$–$C_6$ alkinyl group, a $C_1$–$C_6$ haloalkyl group, or a $C_1$–$C_6$ haloalkenyl group;

m represents an integer of 0 to 4 providing that the plurality of X₂'s may be identical or different from each other where m is 2, 3, or 4;

n represents an integer from 0 to 5 providing the plurality of Y's may be identical or different from each other where n is 2, 3, 4, or 5; and Z represents —CR₂R₃—, —CH₂D, or —CH=CH—, and R₂ and R₃ independently represent a hydrogen atom, a halogen atom, a hydroxy group, a $C_1$–$C_6$ alkyl group, a $C_1$–$C_6$ alkoxy group, a $C_1$–$C_6$ haloalkyl group, a $C_1$–$C_6$ alkylcarbonyloxy group, $S(O)pR_4$, wherein p represents an integer from 0 to 2 and R₄ represents a $C_1$–$C_6$ alkyl group, or a $C_1$–$C_6$ alkylamino group, or R₂ and R₃ jointly represent a hydroxyimino group, a $C_1$–$C_6$ alkoxyimino group, =O, =CH₂ or =NNHR₅, wherein R₅ represents a $C_1$–$C_6$ alkoxycarbonyl group, and D represents CH₂, CO, O, or S.

* * * * *